United States Patent
Bachinski

(10) Patent No.: US 10,166,383 B2
(45) Date of Patent: Jan. 1, 2019

(54) METALLIZED FILM ELECTRODE FOR NONINVASIVE ELECTROTHERAPY

(71) Applicant: EMPI, Inc., Vista, CA (US)

(72) Inventor: Thomas Jerome Bachinski, Lakeville, MN (US)

(73) Assignee: EMPI, Inc., Vista, CA (US)

( * ) Notice: Subject to any disclaimer, the term of this patent is extended or adjusted under 35 U.S.C. 154(b) by 185 days.

(21) Appl. No.: 14/781,018

(22) PCT Filed: Mar. 27, 2014

(86) PCT No.: PCT/US2014/031990
§ 371 (c)(1),
(2) Date: Sep. 28, 2015

(87) PCT Pub. No.: WO2014/160848
PCT Pub. Date: Oct. 2, 2014

(65) Prior Publication Data
US 2016/0045721 A1    Feb. 18, 2016

Related U.S. Application Data

(60) Provisional application No. 61/806,773, filed on Mar. 29, 2013.

(51) Int. Cl.
*A61N 1/04* (2006.01)
*A61N 1/36* (2006.01)

(52) U.S. Cl.
CPC .......... *A61N 1/048* (2013.01); *A61N 1/0452* (2013.01); *A61N 1/0476* (2013.01); *A61N 1/0484* (2013.01); *A61N 1/0496* (2013.01); *A61N 1/36003* (2013.01); *A61N 1/36014* (2013.01)

(58) Field of Classification Search
CPC .... A61N 1/048; A61N 1/0452; A61N 1/0476; A61N 1/0484; A61N 1/0496; A61N 1/36003; A61N 1/36014
See application file for complete search history.

(56) References Cited

U.S. PATENT DOCUMENTS

| | | | |
|---|---|---|---|
| 5,180,379 A * | 1/1993 | Drake | A61N 1/048 439/775 |
| 5,330,526 A | 7/1994 | Fincke et al. | |
| 5,660,892 A * | 8/1997 | Robbins | A61B 5/04087 427/123 |
| 2003/0004558 A1* | 1/2003 | Gadsby | A61N 1/046 607/142 |
| 2003/0074042 A1 | 4/2003 | Gadsby et al. | |

(Continued)

FOREIGN PATENT DOCUMENTS

WO   WO 2009/119383 A1   10/2009

*Primary Examiner* — Catherine Voorhees
*Assistant Examiner* — Natasha Patel
(74) *Attorney, Agent, or Firm* — Knobbe Martens Olson & Bear, LLP

(57) ABSTRACT

Described herein are systems, devices, and methods for providing a metallized film electrode having a metallized film and an electrical connector. The metallized film has a base layer and a metal coating disposed on a bottom surface of the base layer. The metallized film has at least one metal-coated area and may be formed into various shapes for application of therapeutic electrical stimulation to a patient's tissue. The connector provides electrical communication to the first metal-coated area.

19 Claims, 16 Drawing Sheets

(56) References Cited

U.S. PATENT DOCUMENTS

| | | |
|---|---|---|
| 2005/0015134 A1 | 1/2005 | Carim |
| 2010/0057147 A1* | 3/2010 | Fassih ................ A61K 9/0009 607/2 |
| 2011/0077728 A1* | 3/2011 | Li ....................... A61H 39/002 607/152 |
| 2012/0259270 A1* | 10/2012 | Wandke .............. A61N 1/0408 604/23 |
| 2013/0023816 A1 | 1/2013 | Bachinski et al. |

* cited by examiner

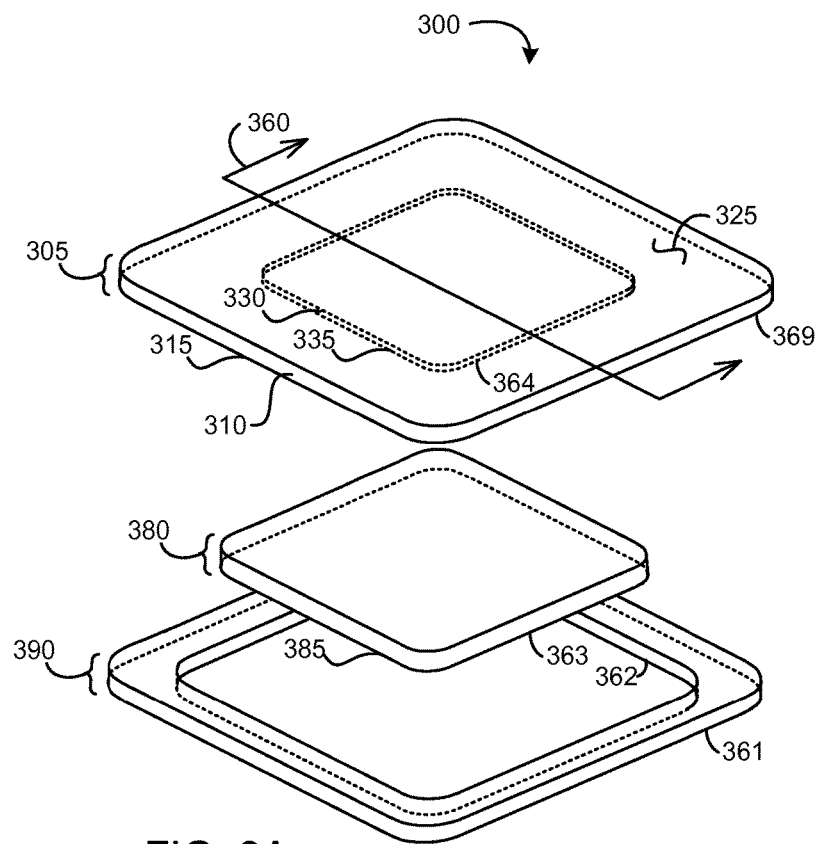
FIG. 3A
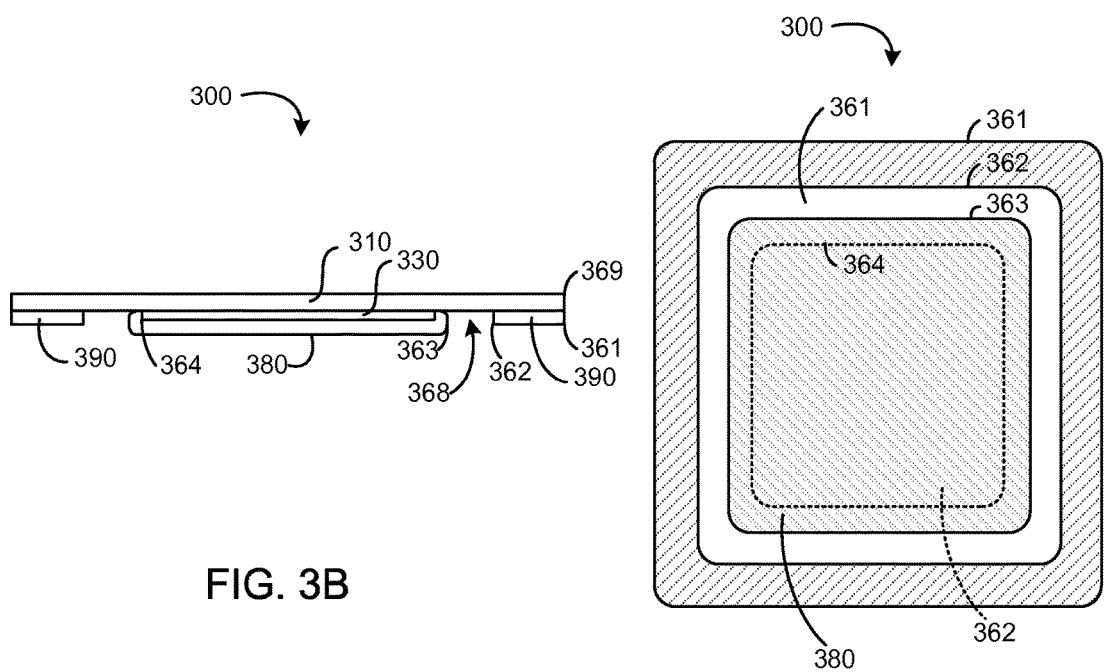
FIG. 3B
FIG. 3C

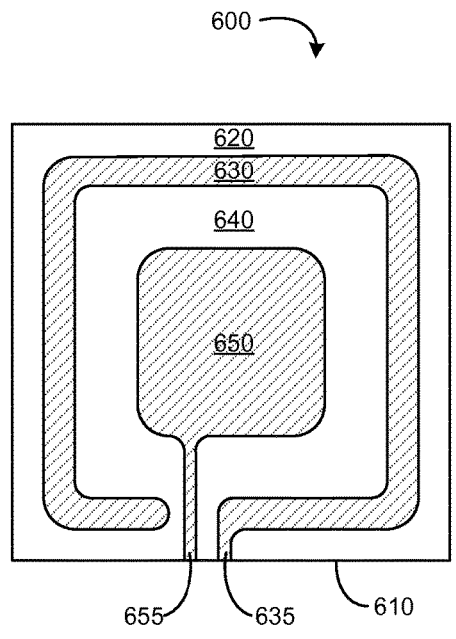
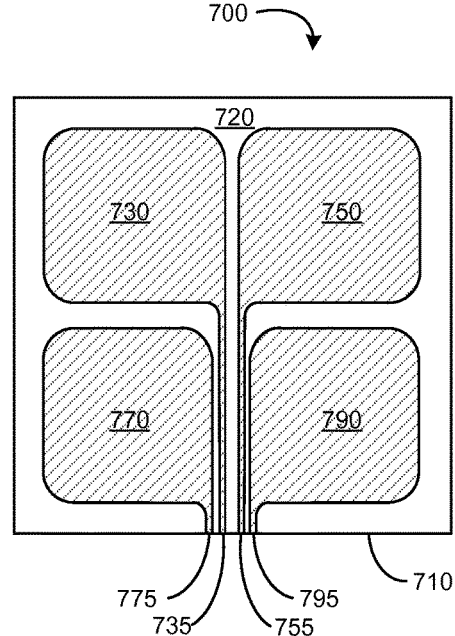
FIG. 6     FIG. 7
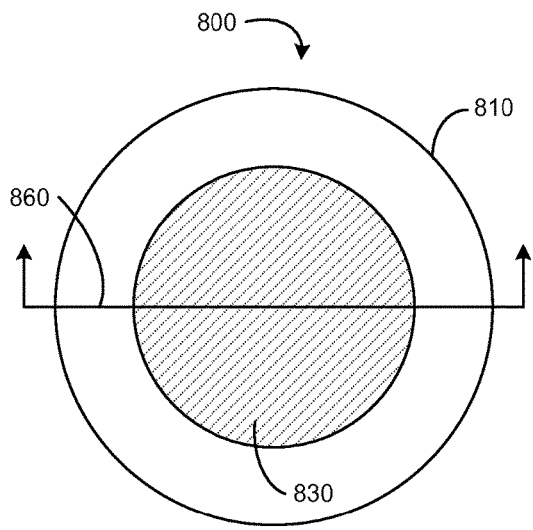
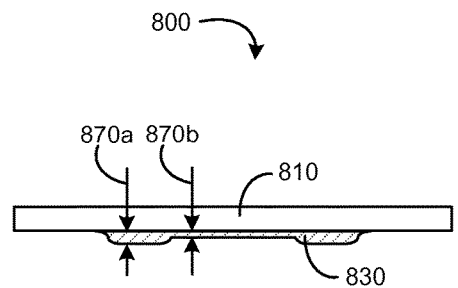
FIG. 8A    FIG. 8B

METALLIZED FILM ELECTRODE FOR NONINVASIVE ELECTROTHERAPY

INCORPORATION BY REFERENCE TO RELATED APPLICATIONS

This application is the national phase under 35 U.S.C. § 371 of prior PCT International Application No. PCT/US2014/031990 which has an International filing date of Mar. 27, 2014, which designates the United States of America, and which claims priority to U.S. Provisional Patent Application No. 61/806,773, filed Mar. 29, 2013. The aforementioned U.S. Provisional Patent Application No. 61/806,773 is incorporated by reference herein in its entirety, and is hereby expressly made a part of this specification.

TECHNOLOGICAL FIELD

This application relates generally to the use and application of electrotherapy devices. More particularly, this application relates to systems and methods for assembling electrodes and electrode connectors for noninvasive electrotherapy.

BACKGROUND

Electrodes are used to apply non-invasive electrotherapy to a patient's body, for example an arm, leg, back or other area where therapy is needed. Therapy is used after in sports or exercise settings to help rehabilitate muscles, and in various applications to help manage pain. Electrodes for noninvasive electrotherapy may have a nonconductive backing layer and an electrical conductive layer for delivering current to the treatment area. During therapy, an adhesive conductive gel layer may be disposed below the conductive layer, against the patient's skin, for secure attachment to the treatment area, and to reduce the impedance at the interface between the conductive layer and the skin. A connector connects the electrode to an electrostimulation device to receive electrical signals for electrostimulation.

SUMMARY

Electrodes used in electrotherapy devices may have "hotspots," which are uneven contact points on the conductive surface, where current builds up in uneven concentrations. Hotspots can disrupt current distribution and can burn the patient. Thus there is a need in the art for improved electrode design.

The devices of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description," one will understand how the features of this invention provide several advantages over current designs.

Disclosed herein are electrodes and electrode connectors for noninvasive electrotherapy, methods of assembling the same, and systems and kits that utilize such electrodes. An electrode thus provided is durable and has a metallized film with appropriate conductivity so it can provide good current dispersion properties, and yet is sufficiently thin such that it can be used with a low-viscosity hydrogel in a low profile.

According to one aspect, a metallized film electrode has a metallized film and a connector. The metallized film has a base layer and a metal coating disposed on a bottom surface of the base layer. The metallized film has a first metal-coated area for application of therapeutic electrical stimulation to a patient's tissue. The connector provides electrical communication to the first metal-coated area. The base layer may be conductive or semi-conductive. In some embodiments, the base layer is polymeric. For example, it may be formed of polyurethane. In some embodiments, the base layer is a woven or a nonwoven fabric. The base layer may be vapor permeable or porous, and the bottom surface of the base layer may include a plurality of dimples or mounds. The metal-coating may comprise pure aluminum, silver, gold, aluminum alloys, or aluminum compounds.

In some embodiments, the electrode has a very thin cross-section. The thin overall cross-section results because the metalized layer and the base layer are both very thin (e.g., the metalized layer is applied atom-by-atom to the film). The cross-section of the metal layer can be measured at a distance between a first point on a bottom surface of the base layer and a second point on the bottom surface of the metal coating which defines a thickness of the metal coating at the first point along a line connecting the first point and the second point that extends vertically through the cross-section at the first point. In certain implementations, the metal coating has a maximum thickness in the range from 0.01 μm to 0.2 μm, or from 0.1 μm to 10 μm. The maximum thickness of the metal coating may be less than 20 μm. In some implementations, the thickness of the metal coating is non-uniform across the first metal-coated area. In certain embodiments, the base layer has a maximum thickness in the range from 0.00001 inches to 0.005 inches, from 0.001 inches to 0.05 inches. The maximum thickness of the base layer may be less than 0.1 inches. This thin construction provides a benefit of increased flexibility and lower cost, compared to currently available electrodes.

According to some implementations, a metallized film electrode may further comprise at least a second metal-coated area spaced apart from the first metal-coated area but in electrical communication with electrostimulation leads. The plurality of metal-coated areas may be electrically isolated and spaced apart.

In some implementations, the base layer further comprises a tail having a third metal-coated area configured as a unitary extension of the first metal-coated area. The width of third metal-coated area may vary from a proximal end of the tail to a distal end of the tail. The third metal-coated area may comprise a connection point that bridges a proximal portion of the third metal-coated area and a distal portion of the third metal-coated area. In certain examples, the connection point is formed by a metal different from the metal coating, such as a separate metal insert or overlay between regions of the tail. The metallized film electrode may further comprise a nonconductive layer disposed along the tail, beneath the third metal-coated area.

In certain embodiments, the connector of the metallized film electrode with a unitary tail is structured with a reinforcement element. In some embodiments that element includes one or more of a conductive wire segment, a metal crimp pin, and a nonconductive housing. Those compounds can be used in combination. For example, the conductive wire segment can be disposed along a proximal end of the tail, wherein at least a portion of the conductive wire segment is in contact with the third metal-coated area. The metal crimp pin has a distal end configured to crimp onto the conductive wire segment and the proximal end of the tail, and a proximal end configured to receive a male pin from an electrostimulation lead. The nonconductive housing is configured to enclose the cylindrical metal crimp pin.

In another example, the connector of the metallized film electrode includes a metal anchor and a lead wire. The metal anchor is disposed beneath the first metal-coated area. The lead wire is configured to provide electrical communication to the metal anchor. The lead wire comprises a metal core and an insulating layer, wherein a first end of the metal core is disposed between the metal anchor and the bottom surface of the first metal-coated area.

In some implementations, the electrode is used with a gel layer disposed beneath the first metal-coated area. The gel layer may be formed of a hydrogel. Because the electrode is thin and disposes current readily, a thinner, less viscous gel can be used. For example, the gel layer may have a maximum thickness in the range from 0.001 inches to 0.1 inches, or from 0.005 inches to 0.05 inches and in one example, is 0.035 inches. In some implantations, the gel is disposed in a container and applied as a roll-on or spray. According to different embodiments, a combined thickness of the metallized film and the gel layer has a maximum value in the range from 0.001 inches to 0.05 inches, or from 0.005 inches to 0.1 inches, and in some aspects, may be 0.036 inches.

According to another aspect, an electrode system for noninvasive electrotherapy may comprise a metallized film electrode as disclosed above, and a hydrogel suitable for roll-on or spray-on applications.

According to another aspect, a method for assembling a metallized film electrode for noninvasive electrotherapy is provided (as is the film, as made by the method), the method comprising providing a metallized film by physical vapor deposition of a metallic material onto a bottom surface of a base layer, and applying a connector to the metallized film electrode. The metallized film is configured to have a first metal-coated area for application of therapeutic electrical stimulation to a patient's tissue. The connector is applied to the first metal-coated area for electrical communication. According to various embodiments, the base layer may be nonconductive or semi-conductive. In some embodiments, the base layer is polymeric. The metal-coating may be pure aluminum. In some embodiments, the method for assembling a metallized film electrode further comprises providing a mask to intercept or block the vaporized metallic material and to produce uncoated areas on the base layer.

According to certain implementations, a connector is formed to the first metal-coated area by forming a tail to the metallize film, wherein the tail has a second metal-coated area configured as a unitary extension of the first metal-coated area, and disposing a nonconductive layer along the tail, beneath the second metal-coated area. According to other implementations, the connector is formed to the first metal-coated area by first disposing a conductive wire segment along a proximal end of the tail, wherein at least a portion of the conductive wire segment is in contact with the second metal-coated area, then crimping a distal end of a metal crimp pin onto the conductive wire segment and the proximal end of the tail, wherein a proximal end of the metal crimp pin is configured to receive a male pin from an electrical stimulation lead, and enclosing the cylindrical metal crimp pin with a nonconductive housing.

According to another aspect, a method for applying electrotherapy is provided the method includes providing a metallized film electrode, applying a layer of hydrogel to the surface of a patient's skin with a hydrogel dispenser, adhering the first metal-coated area of the metallized film electrode to the hydrogel layer by pressing the metalized polymer film against the patient's tissue, and delivering electrical stimulation waveforms to the metallized film electrode through the connector.

According to another aspect, a metallized film electrode kit is provided with a portion, such as a roll or a sheet of metallized film, an anchor connector, and a hydrogel dispenser. The metallized film may comprise a base layer and a metal coating disposed on a bottom surface of the base layer. The anchor connector may comprise a metal anchor and a lead wire; the lead wire having a metal core and an insulating layer. A first end of the metal core is disposed on a top surface of the metal anchor.

According to another aspect, a method of applying electrotherapy is provided. The method may comprise providing a metallized fabric, wherein the metallized fabric comprises a fabric base layer and a metal coating disposed on a bottom surface of the base layer. The method may further comprise tailoring a wearable garment electrode from the metallized fabric, wherein the metal coating is on an inner surface of the wearable garment electrode. The method may further comprise applying a connector to the metal coating for electrical communication, and delivering electrical stimulation waveforms to the wearable garment electrode through the connector, wherein a hydrogel may be disposed under at least a portion of the metal coating.

According to another aspect, an electrode system for noninvasive electrotherapy is provided, comprising an electrode as described herein and a hydrogel suitable for roll-on application.

According to another aspect, an electrode system for noninvasive electrotherapy is provided, comprising an electrode as described herein and a hydrogel suitable for spray-on application.

According to another aspect, an electrode for noninvasive electrotherapy is provided, comprising any of the characteristics described herein.

According to another aspect, a method of assembling electrode for noninvasive electrotherapy is provided, comprising any of the characteristics described herein.

According to another aspect, a method of applying noninvasive electrotherapy is provided, comprising any of the characteristics described herein.

Variations and modifications will occur to those of skill in the art after reviewing this disclosure, where disclosed features may be implemented in any combination and sub-combinations (including multiple dependent combinations and subcombinations), with one or more other features described herein. The various features described or illustrated above, including any components thereof, may be combined or integrated in other devices, systems, or methods; moreover, certain features may be omitted or not implemented. Any of the features of an aspect, embodiment, or implementation is applicable to all other aspects, embodiments, or implementations identified herein. Moreover, any of the features of an aspect, embodiment, or implementation independently combinable, partly or wholly with other aspects, embodiments, or implementation described herein in any way, e.g., one, two, or three or more embodiments may be combinable in whole or in part. Further, any of the features of an aspect, embodiment, or implementation may be made optional to other aspects, embodiments, or implementation. Any aspect, embodiment, or implementation of a method can be performed by a system or apparatus of another aspect, embodiment, or implementation, and any aspect, embodiment, or implementation of a system can be configured to perform a method of another aspect, embodiment, or implementation.

BRIEF DESCRIPTION OF THE DRAWINGS

These and other features, aspects, and advantages of the present invention will now be described in connection with embodiments of the present invention, in reference to the accompanying drawings. The illustrated embodiments, however, are merely examples and are not intended to limit the invention.

FIGS. 3A, 3B, and 3C are exploded, cross-sectional, and bottom views of a metallized film electrode, according to an exemplary implementation;

FIGS. 6 and 7 are bottom views of metallized film electrodes with a plurality of metal-coated areas, according to an exemplary implementation;

FIGS. 8A and 8B are bottom and cross-sectional views of a metallized film electrode with a non-uniform metal coating, according to an exemplary implementation;

DETAILED DESCRIPTION

Figure 1A:
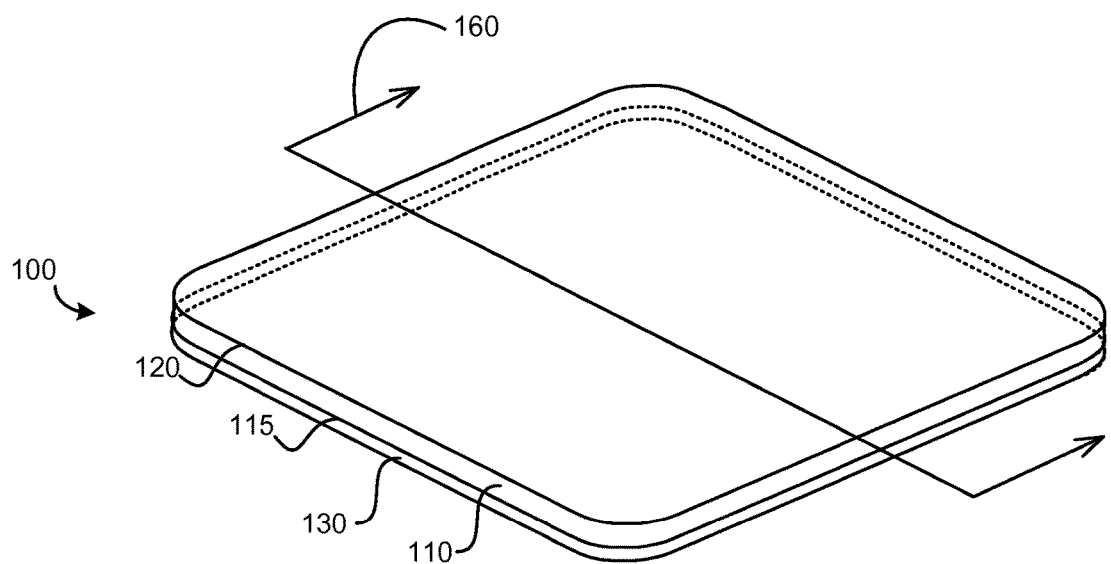
FIGS. 1A and 1B are perspective and cross-sectional views of a metallized film electrode, according to an exemplary implementation.

Any feature or combination of features described herein are included within the scope of the present disclosure provided that the features included in any such combination are not mutually inconsistent as will be apparent from the context, this description, and the knowledge of one skilled in the art. In addition, any feature or combination of features may be specifically excluded from any embodiment of the present disclosure. For purposes of summarizing the present disclosure, certain aspects, advantages, and novel features of the present disclosure are described herein. Of course, it is to be understood that not necessarily all such aspects, advantages, or features will be present in any particular embodiment of the present disclosure.

It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

To provide an overall understanding of the systems, devices, and methods described herein, certain illustrative embodiments are described. For the purpose of clarity and illustration, these systems, devices, and methods are described with respect to electrodes and electrode systems for electrotherapy. It will be understood by one of ordinary skill in the art that the systems, devices, and methods described herein may be adapted and modified as appropriate. These systems, devices, and methods may be employed in other suitable applications, such as for other types of electrotherapy, and other such additions and modifications will not depart from the scope hereof. It will be understood by one of ordinary skill in the art that figures describe herein are not drawn to scale.

Electrodes, such as those disclosed herein, may be used to apply non-invasive electrotherapy to a patient's body, for example an arm, leg, back or other area where therapy is needed. Certain applications of electrodes may result in "hotspots" on the patient's skin. A hotspot is caused by electrode contact points having an uneven distribution or concentration of (electrical) energy on the conductive surface of the skin, often resulting can burn superficial burns.

Some electrodes may cause hotspots on the patient's skin when applied for use during electrotherapy. To aid current dispersion over the surface of the electrode, some techniques use metal plates, metal foils, or polymers impregnated with conductive particles such as carbon as the conductive layer of the electrode. However, these techniques may not adequately address the "hotspot" problem, and in many cases result in further negative consequences.

For example, metal plates have very good conductivity for fast and even current dispersion over the surface of the electrode and low impedance to facilitate low-intensity signal output from the electrostimulation device. However, metal-plate electrodes may be quite thick (e.g. about 200 µm or greater) and thus may not be sufficiently flexible for application to many body areas, and can intermittently lose contact with the treatment area, especially when muscle contraction and flexion occur as a result of electrostimulation. Corresponding changes in the contact surface area may lead to hotspots, where high current densities passing through small or concentrated areas of the patient's tissue may cause stinging, tingling, or burning sensations. Metal-plate electrodes may further be expensive and difficult to manufacture for use under different treatment schemes on different parts of the body.

Metal foil electrodes may be light-weight and flexible enough to be shaped according to some contours of the treatment area, but the metal foil may be prone to delamination from the non-conductive backing layer during use and subsequently generates hotspots. More specifically, a metal foil such as silver or aluminum may generally be adhesively attached, laminated, or pressed to a pliable non-conductive backing layer to form a rolled material, from which electrodes are cut. Because the metal foil and the nonconductive layer are bounded on a macroscopic scale, this process can leave gaps and irregularities in the interface between the backing layer and conductive surface, which can reduce the adhesion strength between the two layers. Additionally, although metal foils are thinner than metal plates, they are usually quite fragile and prone to tear and wear. In some cases, the metal foil layer starts to delaminate during a simple use. Such irregularities can also cause undesirable hotspots.

In addition to metal plates and metal foils, conductive polymer inks impregnated with conductive particles such as carbon may commonly be used to form the conductive layer of some electrodes for noninvasive electrotherapy. Conductive-ink electrodes are flexible and cost effective in some situations, and can be printed into different shapes and patterns, yet they have a number of drawbacks. Conductive inks use chemical solutions or mixtures, which may be inherently less conductive than metals. As a result, conductive-ink electrodes often do not disperse current as readily or evenly as metal-plate or metal-foil electrodes. A metal snap or pigtail connector may be required to be attached to a top or bottom surface of the conductive layer, away from the gel layer, to avoid directly forming a hotspot at the point of attachment of the connector. Even then, current density at the point of attachment of the connector is generally higher than current densities along the periphery of the electrode. Uneven current dispersion, extensive degradation of conductivity over time, and having a nonmetal-metal interface with the connector can all increase the likelihood of hotspots. Furthermore, conductive inks have higher impedances than metal plates and metal foils. To overcome such high impedance values to deliver currents, electrostimulation signals may need to have high intensities, thus potentially compromising patient comfort and safety.

To offset the effects of hotspots, electrodes may use thick gel layers with high levels of salt or chloride ions to improve the gels' conductivity, but those components significantly may increase the bulk and profile of the electrode, which render it less flexible and unsuitable for wear under clothing. In addition, high salt content may cause electrode and gel corrosion, especially when used for direct current electrostimulation therapies. High salt content may also lead to high gel viscosity and allergic type skin reactions, which can both be undesirable for electrotherapies that are applied over the course of hours or days.

Figure 1B:
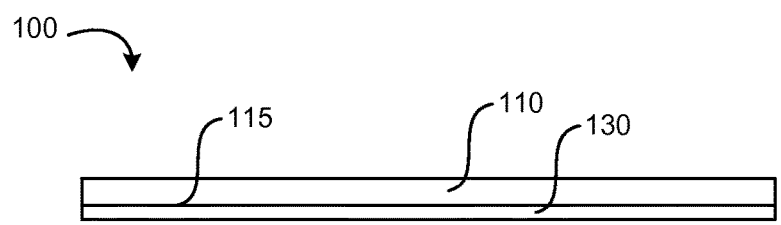

FIG. 1A shows a perspective view of a metallized film electrode 100. FIG. 1B shows a corresponding cross-sectional view of the electrode 100 taken along the line 160. The electrode 100 includes a base layer 110 and a metal coating 130 disposed on a bottom surface 115 of the base layer 110. In an embodiment, the circumference of the metal-coated area is approximately coextensive with the perimeter of the base layer 110. As the name implies, metallized films are obtained by depositing a layer of metal particles on a substrate (not shown). For example, aluminum, silver, or gold coatings can be deposited on the substrate; polymer films, nonwoven fabrics, or woven textiles can serve as the base layer 110. The metal coating 130 may be very thin. In practice, the thickness of a metallized film electrode 100 can be built to be much smaller than other dimensions of the metallized film electrode. Metallized films are thin, yet they are pliable, stretchable, and relatively tear resistant, providing a thin, low-profile, and strong electrode 100 that can help disperse current laterally across the conductive surface. In the metallized film electrode 100, the base layer 110 may be nonconductive and may serve as an insulator to prevent unintentional current delivery through the back of the electrode during electrotherapy.

The metallized film electrode 100 shown in FIGS. 1A and 1B is manufactured by depositing a metallic material onto a substrate. One mode for performing the deposition is physical vapor deposition (PVD). In this technique, a vacuum chamber may be used to avoid reaction of the vaporized material with air. Some gases may be injected into the chamber to form certain types of metal compounds. Vaporized metallic particles are charged, with magnetic and electrical fields configured inside the PVD chamber to filter, purify, and deposit the particle stream onto the substrate. By depositing the metal as particles, the particles can align much more closely together forming atomic bonds with the substrate directly, creating a tight, molecular connection between the metal and the substrate at the interface between the substrate and the metal particles. One beneficial side effect is a stronger bond between the metal coating and the substrate, which helps strengthen the adhesion, and improve resistance to mechanical wear and tear. Another advantage of the PVD process is its ability to produce a very thin (for pliability) and smooth coating along the substrate film. As particles are essentially deposited atom by atom, the thickness and uniformity of the metal coating 130 can be controlled on an atomic level, which helps improve the evenness of current dispersion, thus the resulting electrode 100 is appropriate for use in electrotherapy. Metallized film electrode 100 is thus pliable and resizable, yet still able to maintain low impedances and very good current dispersion properties.

According to various implementations, the base layer 110 may be formed of nonconductive or semi-conductive material, and may comprise a film. Examples may include natural or synthetic polymers such as cotton, nylon, vinyl, polycarbonate, or polyester, including polyurethane, polypropylene, polyethylene terephthalate (PET), and Mylar, or various composites. Fiber-reinforced polymers or fabrics woven from nonconductive fibers or yarns are also possible. The base layer 110 may be transparent or opaque, with or without coloring. A top surface 120 of the base layer 110 may be screen printed with ink, or coated with other materials for further protection of the electrode or for other purposes such as branding.

In some implementations, the base layer 110 may be a continuous solid film formed using a polymer impermeable to moisture vapor and air impermeable. The resulting impermeable base layer 110 may offer some protection against corrosion when the metal coating 130 is formed of a pure active metal, such as aluminum. In some implementations, the base layer 110 may be formed by a porous material that allows water vapor and/or other gas molecules to pass through the material from a bottom surface 115 to the top surface 120 of the base layer 110, thus providing vapor and air permeability.

For example, some low-density polymer materials are inherently porous as a result of monomer linkage structures. Porous permeable materials may also be formed by introducing into raw powder mixtures a pore-forming agent, subsequently removed with heat or chemical treatments once the mixtures are shaped into film substrates. In some other implementations, the base layer 110 may have intermittent perforations across its surface that provide moisture and air permeability. For example, perforations can be formed during the deposition process by shielding certain parts of the substrate with a mask. This is addressed further in the discussions of FIGS. 2A and 17, below. It is also possible to puncture a pre-fabricated metallized substrate to create holes. In an embodiment, a woven fabric substrate may have spacing among the interlaced fibers allowing water and air molecules to pass. The material used to weave the fabric substrate may itself be vapor and air permeable. In some embodiments, the metal coating 130 may be thin and moisture, vapor and air permeable.

Certain embodiments of the electrode 100 having both a permeable base layer 110 and a permeable metal coating 130 may provide breathability and additional user comfort, especially in when utilized in conjunction with a portable electrostimulation device applied to a patient in motion.

As discussed above, the base layer 110 may be a woven or nonwoven fabric. For example, the base layer 110 may be made of spun laid materials that are permeable and/or water absorbent. The base layer 110 may also be a textile woven from nonconductive fibers. One advantage of a fabric base layer as compared to certain types of polymer films is the added tensile strength that allows the electrode to be stretched without breaking. This may be a desirable attribute for reusable electrode 100.

A metallized fabric may be cut directly into electrodes. In addition, a metallized fabric may be tailored into clothing. For example, metallized fabrics can be made into gloves, socks, knee pads, insoles, back belts, or whole pieces of garments such as tank tops and T-shirts. In an embodiment, textile electrodes, such as yarns, may be either interlaced with metallic (e.g., silver) strands or metal-coated before being woven into conductive textiles. An external pull to stretch the conductive textile often causes the silver strands to elongate and break. By comparison, when a textile base layer in a metallized textile electrode is pulled, the metal coating 130 does not necessarily experience the same tensile force, and thus may stay relatively interact to retain its electrical properties.

Figure 18:
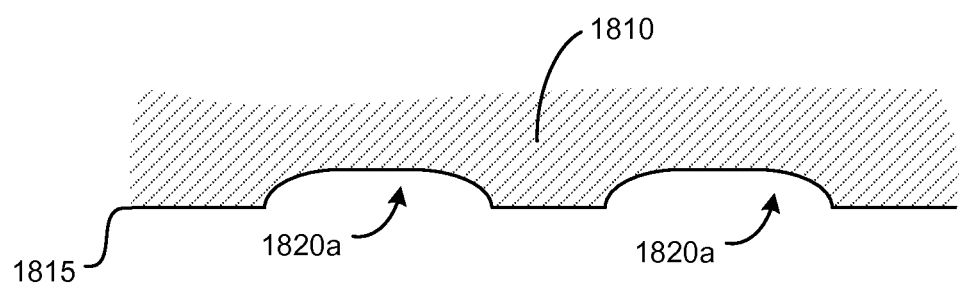
FIG. 18 shows a base layer with dimples, according to an exemplary implementation.
Figure 19:
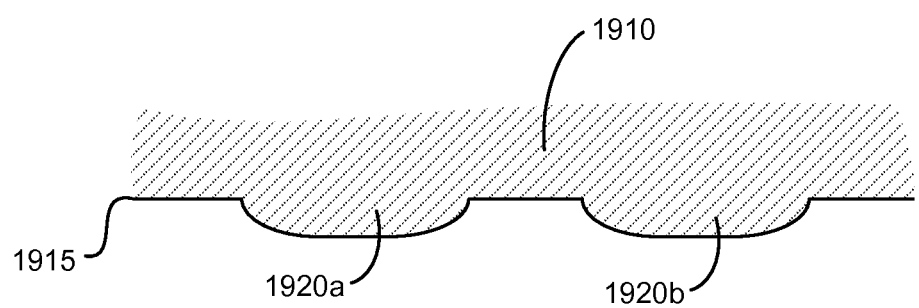
FIG. 19 shows a base layer with mounds, according to an exemplary implementation.

When the base layer 110 is made of a porous material, permeable or impermeable, the presence of a larger surface area at the substrate for metal deposition may further increase adhesion strength between the base layer 110 and the metal coating 130. To increase the surface area for metal deposition, the bottom surface 115 of the base layer 110 may include dimples or mounds or be otherwise textured to increase the amount of surface are in contact with a patient's skin. For example, FIG. 18 shows a cross section of an embodiment of a dimpled base layer 1810. Dimples 1820 and 1830 form one or more troughs on the bottom surface 1815 of the base layer 1810, in contact with the patient's skin. FIG. 19 shows another embodiment where a bottom surface 1915 of a base layer 1910 extends downward at a plurality of positions to form mounds 1920a and 1920b. In different implementations, any number of dimples 1820 or mounds 1920 may be present, in uniform or non-uniform patterns and with uniform or non-uniform spacing. In FIG. 18, the dimples 1820 and 1830 may be oval shaped, with a substantially similar diameter and depth. In FIG. 19, the mounds 1920 and 1930 may also be oval shaped, with a substantially similar diameter and height. In other embodiments, the dimples 1820 and the mounds 1920 may be produced with other shapes, depths, heights, and other relevant parameters. In certain embodiments, the dimples 1820 and the mounds 1920 may be further incorporated in the other embodiments of base layer 115 and analogous structures disclosed herein.

In addition to increasing base layer surface area, the mounded surface 1910 may be used in some applications because the presence of mounds 1920 may allow less metal material to be deposited in forming a metal coating, such as metal coating 130. On the other hand, the dimpled surface 1810 may be used in some applications because the presence of dimples may allow more metal material to be deposited, potentially affecting the impedance of the metal coating 130.

Returning to FIGS. 1A and 1B, according to various examples, the metal coating 130 may be formed of pure aluminum, silver, tin, copper or other metals. In an embodiment, aluminum is an attractive metal for this purpose due to its ease of fabrication, good electrical conductivity, light weight, and low cost. Silver is an attractive option because of its high conductivity and inertness as a noble metal, which makes the electrode less prone to corrosion. As the metal coating 130 may be constructed in very thin sheets, material requests are lower and therefore expensive metals such as silver and gold may be used to produce affordable disposable metallized film electrodes. Alternatively, other metallic materials such as alloys and metal compounds, or other metal-impregnated conductive materials may be deposited as the metal coating 130. Multiple layers of metal coatings 130 are possible, for better adhesion to the substrate, or other desirable mechanical or electrical properties.

The cross-sectional thickness of the metal coating 130 maybe defined at a given first point on the bottom surface of the base layer by considering the distance between the first point on the bottom surface of the base layer and a second point on a bottom surface of the metal coating 130, wherein a line connecting the first point and the second point extends vertically through the cross-section at the first point. In an embodiment, the thickness of the metal coating 130 is considerably smaller than the thickness of the conductive layer in conventional electrodes and may be in any of the ranges from 0.01 µm to 0.2 µm, from 0.1 µm to 1 µm, from 0.1 µm to 10 µm, and in certain examples, is less than 20 µm. By comparison, the thickness of metal-plates or metal-foils in conventional electrodes is typically greater than 50 µm, and often greater than 200 µm. The thickness of the base layer 110 may be in any of the ranges from 0.00001 inches to 0.005 inches; from 0.0001 inches to 0.01 inches; from 0.001 inches to 0.05 inches; and in certain examples, is less than 0.1 inches.

The metallized film electrode 100 shown in FIGS. 1A and 1B has a rectangular shape with rounded corners. In other implementations, metallized film electrodes can take on any shape or size that is appropriate for the treatment being administered, for the location of the treatment site, or for other relevant reasons. For example, a metallized film electrode to be attached to a finger or a toe is likely to be smaller than a metallized film electrode to be attached to a lower back region. A circular electrode may be used in many applications over a square-shaped electrode, for the curved circumference makes it less likely for the electrode to be peeled off or to be lifted. Moreover, since for a given voltage, current density decreases as the surface area of the electrode increases, metallized film electrodes may be cut and reduced in size by a clinician when stronger electrostimulation is desired but the output signal level of the electrostimulation device is limited.

Figure 2A:
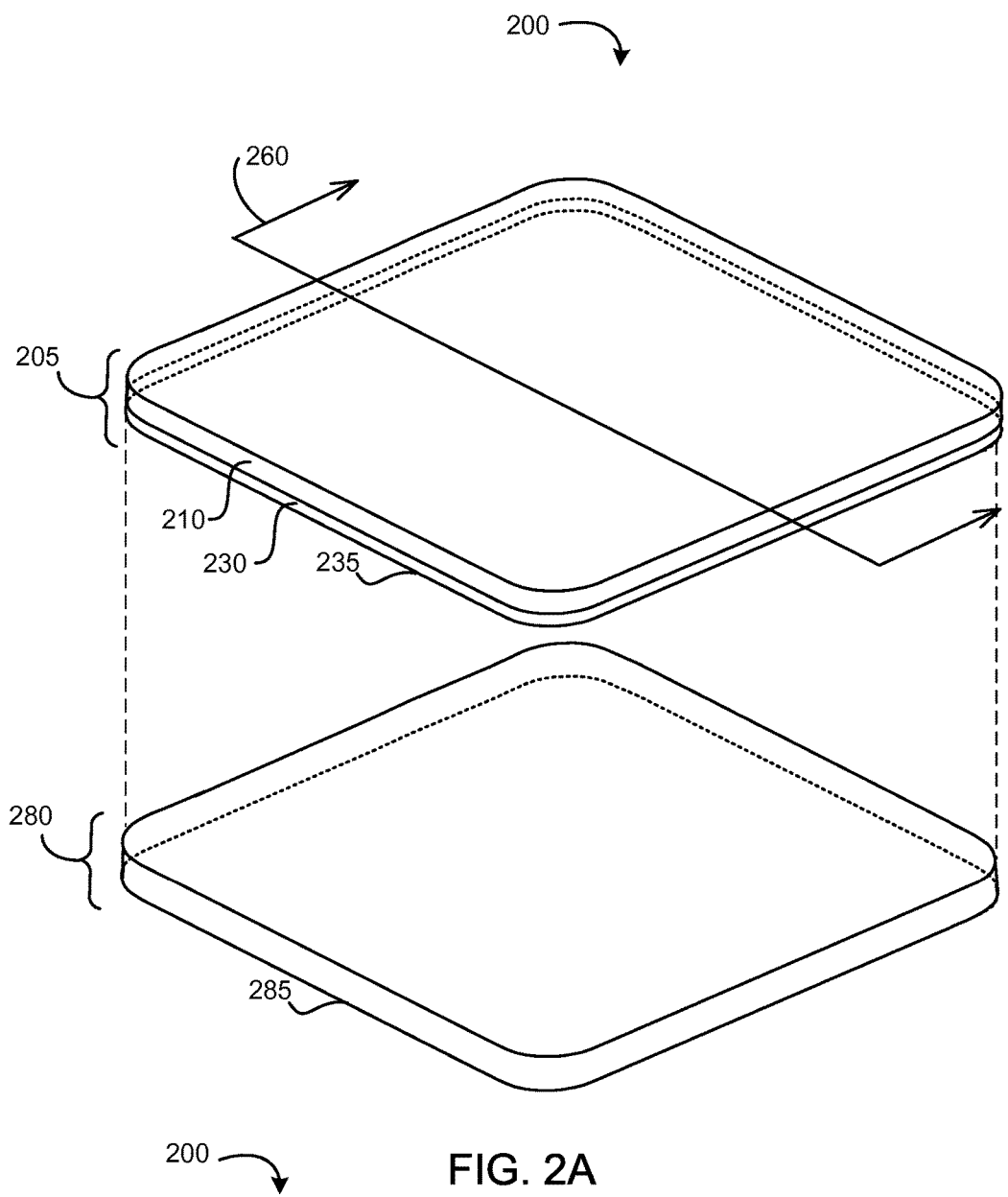
FIGS. 2A and 2B are perspective and cross-sectional views of a metallized film electrode coupled with a gel layer, according to an exemplary implementation.
Figure 2B:
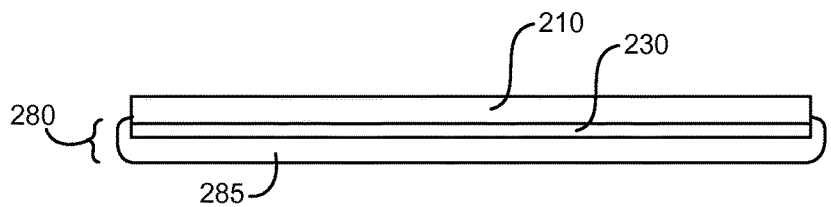

FIG. 2A illustrates an exploded view of a metallized film electrode 200 that includes a gel layer 280 disposed below a bottom surface 235 of the metal coating 230. FIG. 2B shows the corresponding cross-sectional view taken along the line 260. In some embodiments of the present disclosure the gel layer 280 is thin and provides added flexibility to allow the electrode to be placed in constrained areas of the body that are difficult to treat. The relatively thin gels can be used with the electrodes disclosed herein because such electrodes disperse current much more evenly across the surface of the metal coating 230, even when the electrode is bended, stretched, or otherwise shaped according to the contour of the treatment site. Furthermore, as the overall profile and wearability of an electrode may be constrained by gel thickness, metallized film electrodes as disclosed herein may be used with or without thin gel layers to attain a low-profile when applied to the skin, and can be worn under clothing or inside shoes without interfering with the patient's general physical activities or compromising patient comfort. For example, metallized film electrodes can be worn with low-profile portable electrostimulation devices when a patient is sleeping.

In some implementations, the gel layer 280 is pre-fabricated as part of the electrode. A removable release liner (not shown) may be further disposed on a bottom surface 285 of the gel layer 280 to protect the gel layer prior to application to the treatment site. Any of a wide variety of gels may be used in the gel layer 280.

In FIG. 2B, the gel coating 285, contiguous with the gel layer 280, extends around the side of the metallized film 205 to cover the perimeter side surfaces of the metal coating 230. The presence of the gel coating 285 on the perimeter side surfaces of the metallized film 205 helps prevent electrical current from bypassing the gel layer 280 and entering a patient's or clinician's tissue directly, which may cause an uneven distribution of current.

The thickness of the gel layer 280 may be less than 0.1 inches, or less than 0.05 inches. In certain embodiments, the thickness of the gel layer 280 is in any of the ranges from 0.001 inches to 0.1 inches, from 0.005 inches to 0.05 inches, and in certain examples, is about 0.035 inches. The combined thickness of the metallized film 205 and the gel layer 280 may be less than about 0.15 inches. In certain embodiments, the combined thickness is in range from 0.001 inches to 0.05 inches, or from 0.005 inches to 0.1 inches, and in some examples, is 0.036 inches, but may be thinner or thicker as desired in certain designs or implementations.

Another benefit resulting from the even current distribution properties of the metal coating 230 is that the metallized film electrode 200 may be coupled with a hydrogel having low salt content. Ions produced by electrolysis under a direct current driven across the gel may react with the conductive layer. When a hydrogel having low salt content is used with the metallized film electrode 200 as gel layer 280, the electrode and the gel layer are less prone to corrosion, consequently reducing the amount of surface area prone to hotspots or skin reactions (e.g. allergies, skin irritation). Furthermore, low salt content renders the hydrogel more absorbent to water, giving it a less viscous, less sticky consistency. Low viscosity allows hydrogels to be applied in a thinner coat, as compared to conventional hydrogels which do not stretch as easily and often need to be pre-molded into thicker pieces that match the electrodes' shapes.

In some implementations, the gel layer 280 is manufactured entirely separately from the metallized film electrode body 205, and applied with a roll-on, or a spray-on applicator to the treatment area. Some hydrogels may require a short time period to dry; some hydrogels may be fast setting; some hydrogels may take longer to dry. In some implementations, the hydrogel serves as a skin adhesive for the metallized film electrode 200, while some implementations of the metallized polymer film electrode include additional adhesive layers for secure attachment of the electrode to the patient's skin. In some applications, the hydrogel is applied in a thin layer that is less than about 0.1 inches in thickness.

In certain embodiments, the hydrogel layer is between 0.005 inches and 0.05 inches. A further advantage of a dispensable hydrogel is that gel thickness and coverage area can be selected and set by a clinician or the patient according to the type of electrostimulation therapy administered, the output intensity from the electrostimulation device, user preference, or any other relevant factors.

FIG. 3A shows an exploded view of a metallized film electrode 300, according to an illustrative embodiment. FIG. 3B is a cross-sectional view of the metallized electrode 300 of FIG. 3A taken along the line 360 of FIG. 3A. Accordingly, FIG. 3C shows a bottom view of the metallized film electrode 300, according to an illustrative embodiment. All three figures may be referred to in conjunction in the following description.

FIG. 3A shows a metallized film 305 exploded from a gel layer 380. In an embodiment, the metallized electrode 300 further comprises a metal-coated area 330 and a base layer 310. The base layer 310 has smaller dimensions than the base layer 310, leaving an oversized edge portion 325 of the base layer 310 uncoated. Advantageously, the metallized film electrode 300 may be formed having certain areas of the metallized film substrate masked during the fabrication process, creating one or a plurality of regions without a metal coatings, and providing flexibility in electrode 300 design.

To fabricate the metallized film 305, a mask formed according to the oversized edge portion 325 may be placed in between the film substrate and the particle source, from which vaporized particles of metallized materials are emitted. As metal particles travel across the PVD chamber under the influence of electric and/or magnetic fields, particles that come into contact with the mask are intercepted, while particles that reach the film substrate form the metal coating. By configuring the electric and/or magnet fields inside the PVD chamber to control particle trajectory, and by configuring the shape of the mask and the position of the mask inside chamber, the fabricator may achieve a desired coating pattern.

Figure 17:
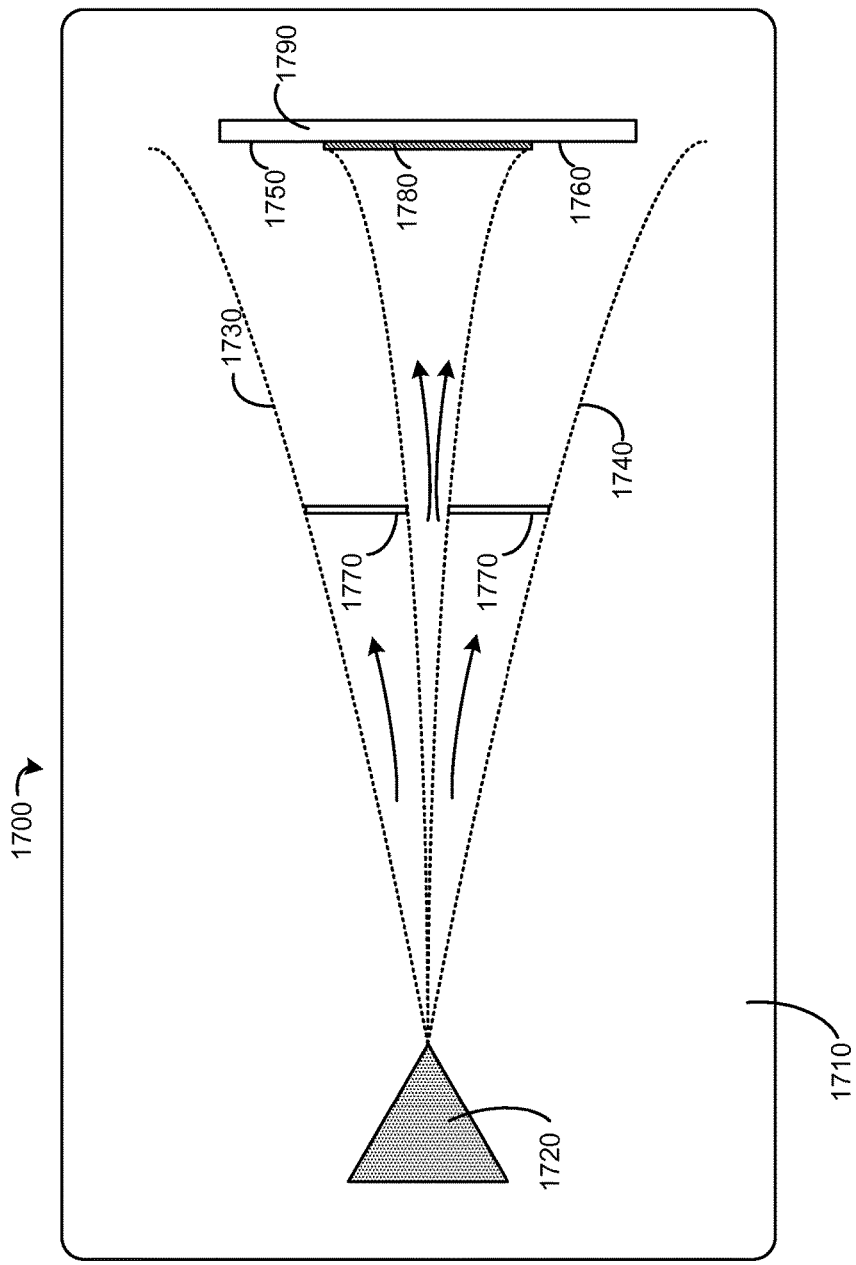
FIG. 17 shows vapor deposition of metal particles to a substrate when a mask is used, according to an exemplary implementation.

As a non-limiting example, FIG. 17 depicts the side view of a deposition system 1700 that includes a particle source 1720, a mask 1770, and a film substrate 1790, all housed in a deposition chamber 1710. The particle source 1720 is located on a first end of the deposition chamber 1710, while the film substrate 1790 is located on a second end of the deposition chamber 1710, opposite to the first end. In an embodiment the mask 1770 is positioned between the particle source 1720 and the film substrate 1790. In this implementation, electric and magnetic fields (not shown) present throughout the interior of the chamber are configured to direct particles emitted by the particle source 1720 toward the film substrate 1790, along paths indicated by the arrows and bounded by a top boundary 1730 and a bottom boundary 1740. Some emitted particles are intercepted by the mask 1770, resulting in uncoated areas 1750 and 1760; the emitted particles not blocked by the mask 1770 are deposited onto the film substrate 1790, forming a metal-coated area 1780. It is to be understood by one of ordinary skill in the art that FIG. 17 is a representative illustration of a deposition system, and not drawn to scale. In practice, the mask 1770 may be positioned further away or closer to the film substrate 1790; the mask may also be disposed directly on top of the film substrate, and may be mechanically removed, peeled off, or chemically washed from the film substrate 1790 after the deposition process.

Returning to FIG. 3A and FIG. 3B, the oversized edge 325 allows increased skin contact and provides an additional protection against current leakage through edges of the electrode, when the electrode is touched by the patient or a clinician during therapy. The metal-coated area 330 is disposed on a bottom surface 315 of the base layer 310, and the gel layer 380 is disposed beneath a bottom surface 335 of the metal-coated area 330. The gel layer 380 may extend beyond the perimeter of the metal-coated area 330 to prevent unintentional direct contact of the metal-coated area 330 with the patient's skin. In some embodiments, the gel layer 380 is pre-fabricated as part of the electrode. In some embodiments, a hydrogel with low viscosity is applied using a hydrogel dispenser. An additional adhesive peripheral layer 390 may be disposed directly beneath the bottom surface 315 of the base layer 310, around the gel layer 380. The presence of the adhesive peripheral layer 390 ensures secure attachment of the electrode to the skin, and may prevent the gel layer 380 from extending beyond the treatment area when external pressure is unintentionally applied to the back of the electrode, especially when a low-viscosity hydrogel is used.

FIG. 3C shows a bottom view of the metallized film electrode 300, illustrating the relative dimensions of the film base layer 310, the metal-coated area 330, the gel layer 380, and the adhesive peripheral layer 390. A perimeter 363 of the gel layer 380 extends beyond a perimeter 364 of the metal-coated region 330 (shown in dashed lines) to prevent electrical current from bypassing the gel layer 380, entering a patient's tissue directly, and causing "edge stings." An outer perimeter 361 of the adhesive peripheral layer 390 coincides with a perimeter 369 (FIG. 3B) of the base layer 310 to prevent the electrode from being unintentionally peeled off the treatment area.

In an embodiment, the adhesive peripheral layer 390 does not overlap with the gel layer 380, creating a small circumferential gap 368 (FIG. 3C) between the perimeter 363 of the gel layer and an inner perimeter 362 of the adhesive peripheral layer 390. The small circumferential gap 368 may be created as a result of a manufacturing process, when both the gel layer 380 and the adhesive peripheral layer 390 are pre-fabricated and included as part of the metallized film electrode 300. The small circumferential gap may also be put in to allow the base layer 305 to taper off the gel layer 380 towards the patient's skin when a pre-molded, thick, viscous gel is used for the gel layer 380. As a result, the adhesive peripheral layer 390 may be less likely to crease, wrinkle, and/or stick to itself. In some other embodiments, the inner perimeter 362 of the adhesive peripheral layer 390 may be in direct contact with the perimeter 363 of the gel layer 380. In some embodiments, the perimeter 363 of the gel layer 380 may extend at least partially beyond the inner perimeter 362 of the adhesive peripheral layer 390. For example, when a hydrogel is rolled-on from a gel bottle, the shape of the gel spread may be irregular, and the gel layer 380 may extend at least partially into the adhesive peripheral layer 390 or beyond the perimeter 369 of the base layer 305. In some implementations, adhesive peripheral layers shaped to cover the entire perimeter 369 of the base layer 305 may serve as a gel guard to prevent hydrogels from being squeezed out of the treatment area when pressure is applied from the back of the electrode, for example, when the patient lies on the electrode during sleep.

In some implementations, the adhesive peripheral layer 390 is pre-fabricated to be included as part of the metallized film electrode 300. In some implementations, the adhesive peripheral layer 390 takes the form of a double-sided non-conductive tape and is manufactured separately from the metallized polymer film 305 and the gel layer 380.

Figure 4:
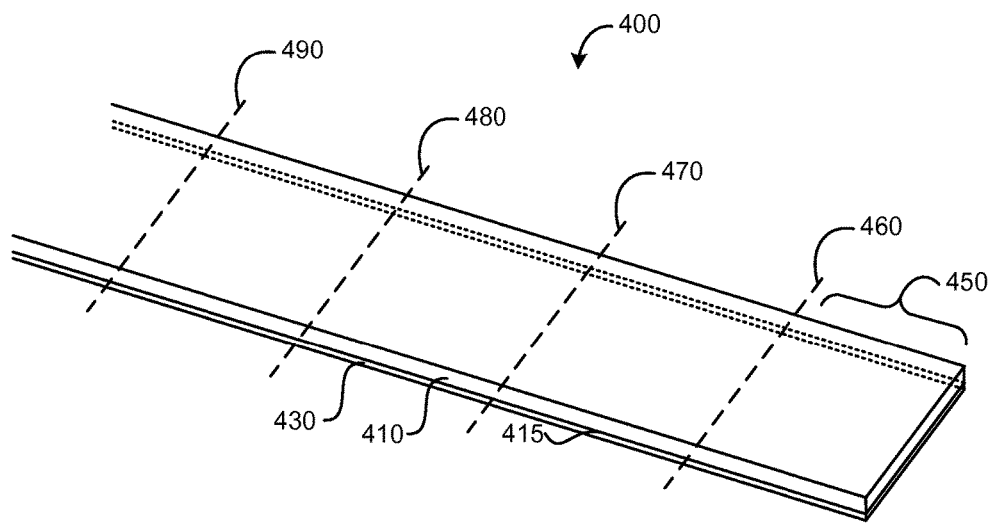
FIGS. 4 and 5 are perspective views of metallized film strips, according to an exemplary implementation.
Figure 5:
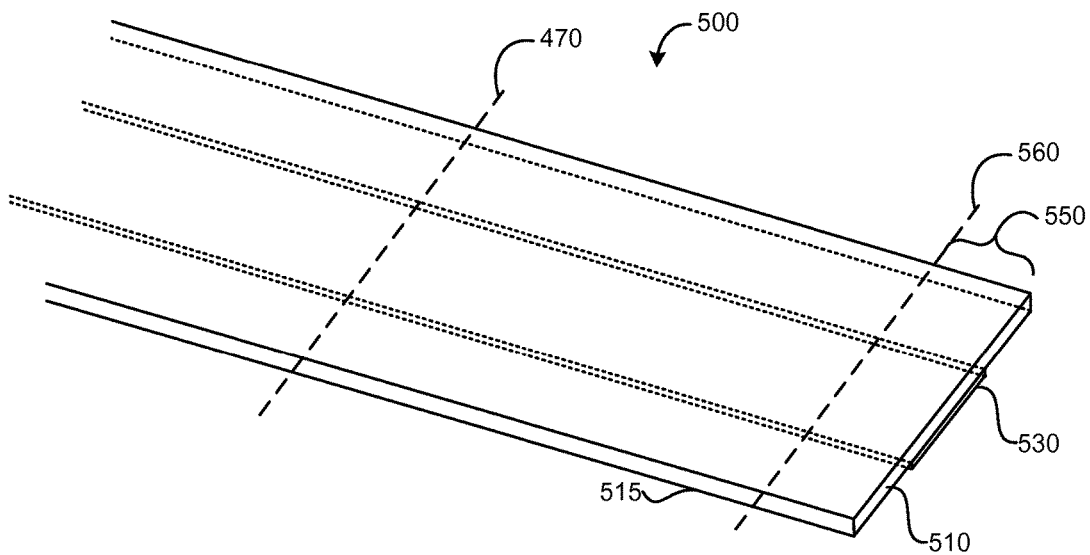

FIG. 4 and FIG. 5 show perspective views of metallized film strips 400 and 500, respectively that can be custom-cut into electrodes, according to different illustrative embodiments. In FIG. 4, the metal-coated area 430 is coextensive in dimension with the polymer base layer 410, with the metal coating 430 covering the entire bottom surface 415 of the base layer 410. A metallized film electrode 450 similar to the one shown in FIG. 1A may be formed from the metallized film strip 400 shown in FIG. 4 by a cut along the line 460 located near an end of the metallized film strip 400. Multiple metallized film electrodes 450 may similarly be cut from the metallized film strip 400 by cutting along the lines 470, 480, 490.

In FIG. 5, a metal-coated area 530 is narrower in width than the base layer 510, with the longitudinal center line of the metal-coated area 530 aligned with the longitudinal center line of the base layer 510. Adhesive strips (not shown) may be further disposed on the uncoated portions of the bottom surface 515 of the base layer 510, on both sides of the metal-coated area 530, so that a metallized film electrode 550 obtained by cutting along the line 560, near one end of the metallized film strip 500, has the shape of a typical adhesive bandage and can be wrapped around a body part such as a finger. In some implementations, the metallized film strips 400 and 500 are packaged into rolls for easy dispensing. Perforations may be further formed into the strips 400, 500 to enable individual electrodes of pre-defined sizes to be easily torn away. For example, in the embodiment shown in FIG. 4 above, perforation holes may be located along uniformly spaced parallel lines 460, 470, 480, and 490. Individual electrodes can thus be torn out one by one, starting from a loose end of the roll of metallized film strips.

In some implementations, metallized film electrodes described herein can be cut by a clinician or patient from the metallized film sheets (not shown) into different shapes that fit particular treatment areas or achieved certain desired current densities. For example, an elongated piece may be appropriate when the electrode is to be wrapped around a patient's lower leg, and an electrode with a large metal-coated area may be desirable when the current density as needed by the electrostimulation therapy is very low.

FIG. 6 shows a bottom view of a metallized film electrode 600, according to an illustrative embodiment, with a plurality of disconnected metal-coated areas, a first metal-coated area 630 and a second metal-coated area 650, deposited on a base layer 610. As discussed with reference to FIG. 2A and FIG. 17, a mask 1770 may be configured to intercept vaporized metal particles to produce uncoated areas on the substrate. By alternating the shaped of the mask, different coating patterns may be created. In the metallized film electrode 600, the base layer 610 has an uncoated circumferential rim 620 around its perimeter. Inside and adjacent to the circumferential rim 620 is the first metal-coated area 630, a circumferential strip with an extended portion 635 reaching to the outer perimeter of the base layer 610. A second metal-coated area 650 is substantially square shaped, with an extended portion 655 also reaching to the outer perimeter of the base layer 610. The first metal-coated area 630 and the second metal-coated area 650 are disconnected and spaced apart by the uncoated area 640. The first metal-coated area 630 may comprise a first type of metallic material such as a pure metal, an alloy, or a metal compound. The second metal-coated area 650 may comprise the same first type of metallic material, or a second type of metallic material, different from the first type of metallic material. The extended portions 635 and 655 serve as conductive leads to the metal-coated areas 630 and 650 respectively, and may be electrically connected through separate connectors to electrical output from an electrostimulation device. The electrode 600 is compatible with two-channel interferential electrostimulation and TENS therapy, among others. When in use, separate gel segments (not shown) may be coupled with the plurality of metal-coated areas, while additional adhesive tapes (not shown) or straps may be used to secure the electrode to the treatment area. Nonconductive adhesive tapes may be disposed under the uncoated area 620 to secure the electrode and to prevent unintentional current leakage through the edges of the electrode 600. Nonconductive adhesive tapes may also be disposed under the uncoated area 640 to secure the electrode and to insulate the coated areas 630 and 650 from short circuiting, which may occur when separate gel layers disposed below the coated areas 630 and 650 accidentally touch, causing current to flow through the gel from one coated area to the other instead of through the patient's tissue.

According to various embodiments, any number of metal-coated areas may be deposited on the non-conductive base layer, by configuring the shape, size, and location of the mask (see discussion with reference to FIG. 17).

FIG. 7 shows a bottom view of another metallized film electrode 700, according to an illustrative embodiment, with a plurality of square-shaped, disconnected metal-coated areas 730, 750, 770, and 790 deposited on a base layer 710. The metal-coated areas 730, 750, 770 and 790 are arranged as a two-by-two grid, positioned inside an uncoated circumferential rim 720 around the perimeter of the base layer 710. In this embodiment, each of the plurality of metal-coated areas has an extended portion, 735, 755, 775, and 795, that may serve as conductive leads to each of the metal-coated areas respectively and may be electrically connected through separate connectors to an electrostimulation device.

FIG. 8A shows a bottom view of a circular metallized film electrode 800, according to an illustrative embodiment, with a metal-coated area 830 deposited on a base layer 810. In an embodiment, the metal-coated area 830 has a non-uniform thickness 870, as shown in FIG. 8B. FIG. 8B is a cross-sectional view, taken along the line 860 of FIG. 8A. The thickness 870 is shown as first thickness 870a and second thickness 870b, the second thickness 870b having a thinner dimension than first thickness 870a. The thickness 870 of the metal coating may be controlled during the PVD process by adjusting deposition speed. The thickness 870 of the metal-coated area 830 may vary around its perimeter to allow an electrical current drop-off (e.g., a current reduction) and reduce edge biting and stinging. Thickness of the metal-coated area 830 may also be configured according to the type of connector used and the location of connector attachment, with impedance matching to ensure even current distribution over the surface of the electrode.

To establish electrical connection to an electrostimulation device, a metallized film electrode may further comprise a connector electrically coupled to the metal coating (e.g., the metal-coated are 830). As a non-limiting example, snap connectors, inverted snap connectors, and magnetic connectors similar to those disclosed in PCT Publ. No. WO2013/012465, the contents of which are hereby incorporated by reference in their entirety, may be used. Conventional electrodes with a separate nonconductive backing layer and a conductive layer are often formed with additional metal connective components such as snap receptacles or magnetic foils inserted between the two layers. Such connective components are in direct contact with the conductive layer as well as lead wires from the electrostimulation device. Generally, these connective components are not placed below the conductive layer, in direct contact with a gel layer; such a configuration may cause hotspots where the impedance of the conductive layer becomes relatively high.

In metallized film electrodes such as those disclosed herein, metal connective components (not shown) may be placed on the base layer, before metal coatings are deposited during the PVD process, to establish connectors similar to those present in conventional electrodes. In addition, good current dispersion properties of the metal coating allow connective components to be attached to a bottom surface of the metal coating directly.

Figure 9A:
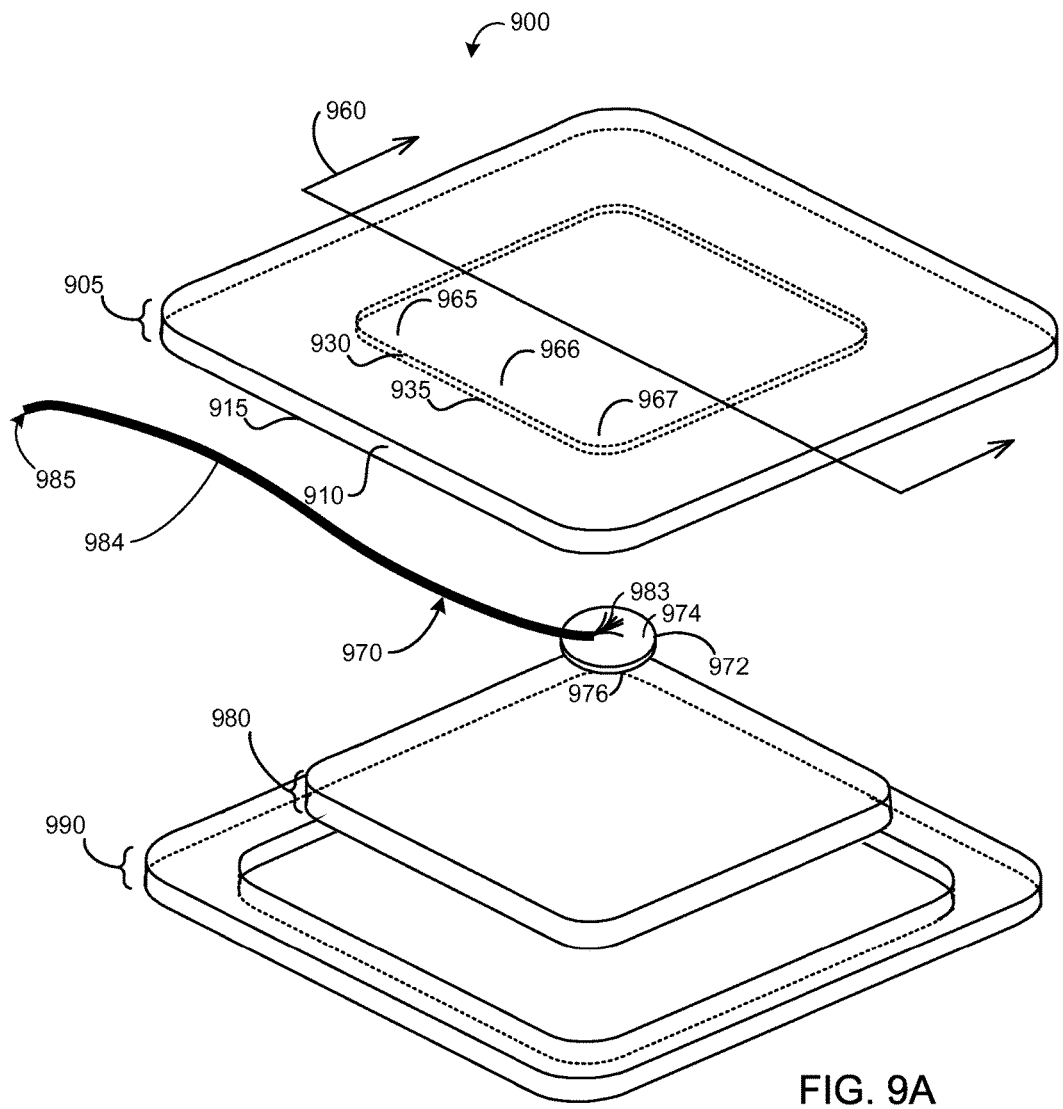
FIGS. 9A and 9B are exploded and cross-sectional views of a metallized film electrode with an anchor connector, according to an exemplary implementation.

FIG. 9A is an exploded view of an illustrative metallized film electrode 900 with an anchor connector 970. The electrode 900 comprises a metallized film 905, an anchor connector 970, a conductive gel layer 980, and an adhesive peripheral layer 990. In an embodiment, the metallized film 905 comprises a base layer 910 and a metal coating 930 disposed on a bottom surface 915 of the base layer 910. The materials and arrangements of the metallized film 905, the gel layer 980, and the adhesive peripheral layer 990 are described with reference to the metallized film electrode in FIGS. 3A and 3B but can be applied to any of the embodiments of this disclosure. The anchor connector 970 further comprises a thin metal anchor 972 and a lead wire 984. The metal anchor 972 may be a metal plate or foil made of the same type of metallic material as that used for the metal coating 930. The use of a metallic material for the metal anchor 972 helps drive current input from the lead wire 984 through a path of least resistance (e.g., minimal impedance) to the metal coating 930, instead of the gel layer 980. After being dispersed across the surface of the metal coating 930, the current is delivered through the gel layer 980 to the patient's skin.

In the embodiment shown in FIG. 9A, a distal end of the lead wire 984 is disposed between a top surface 974 of the metal anchor 972 and a bottom surface 935 of the metal coating 930. The lead wire 984 may comprise a metal core enclosed in a layer of insulation. The metal core may be a flat metal strip, a solid single-strand wire, or a multi-strand bundle of smaller gauge wires wrapped together inside the insulation layer. In the embodiment shown in FIG. 9A, the lead wire 984 is multi-stranded. The distal end of the lead wire 984 has the insulation layer removed to expose strands of wires 983 inside. The exposed strands of wires 983 may be fanned before being disposed between the top surface 974 of the metal anchor 972 and a bottom surface 935 of the metal coating 930. In some embodiments, the strands of wires 983 on the distal end of the lead wire 984 are soldered to the metal anchor 972, and the metal anchor 972 is further soldered to the metal coating 930. In some embodiments, the strands of wires 983 on the distal end of the lead wire 984 are attached adhesively to the top surface 974 of the metal anchor 972, and the metal anchor 972 is further attached adhesively to the bottom surface 935 the metal coating 930. The proximal end 985 of the lead wire 984 may include a female socket (not shown) to receive a male lead pin connected to an electrostimulation device.

Figure 9B:
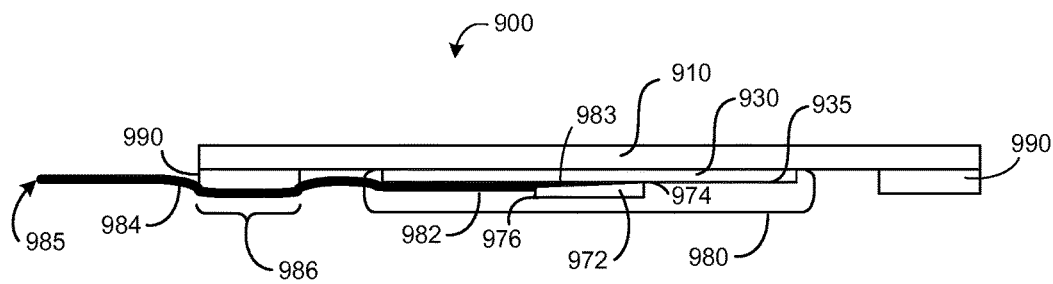

FIG. 9B shows a cross-sectional view of the illustrative metallized film electrode 900 taken along the line 960 of FIG. 9A. The strands of wires 983 on the distal end of the lead wire 984 are disposed between the bottom surface 935 of the metal coating 930 and the top surface 974 of metal anchor 972. In some embodiments, the metal anchor connector 970, including the lead wire 980 and the anchor 972, is prefabricated to be included as part of the metallized film electrode 900. In the implementation shown in FIG. 9B, the metal anchor 972 is soldered to the metal coating 930, with the strands of wires 983 on the distal end of the lead wire 984 disposed between the bottom surface 935 of the metal coding 930 and the top surface 974 of the metal anchor 972. The proximal end 985 of the lead wire 984 extends beyond the perimeter of the electrode 900 and may include a female socket (not shown) configured to receive a male pin (not shown) connected to an electrostimulation machine, or a male pin configured to couple with a female socket connected to an electrostimulation machine. In the embodiment shown in FIG. 9B, a portion 986 of the lead wire 984, between the distal end and proximal end 985 of the lead wire 984, is disposed below the adhesive peripheral layer 990. In some embodiments, the portion 986 of the lead wire 984 is disposed between the base layer 910 and the adhesive peripheral layer 990 (not shown).

In the embodiment shown in FIGS. 9A and 9B, the metal anchor 972 of the anchor connector 970 is disposed approximately at the center of the metal-coated area 930. In other embodiments, the metal anchor 972 may be disposed anywhere within the boundaries of the metal-coated area 930. For example, the metal anchor may be disposed at around corners 965 or 967, or near a midsection 966 of an edge of the metal-coated area 930. In embodiments where the metallized film electrode takes on other shapes, the metal anchor may be similarly disposed anywhere within the boundary of the metal-coated areas.

Figure 10A:
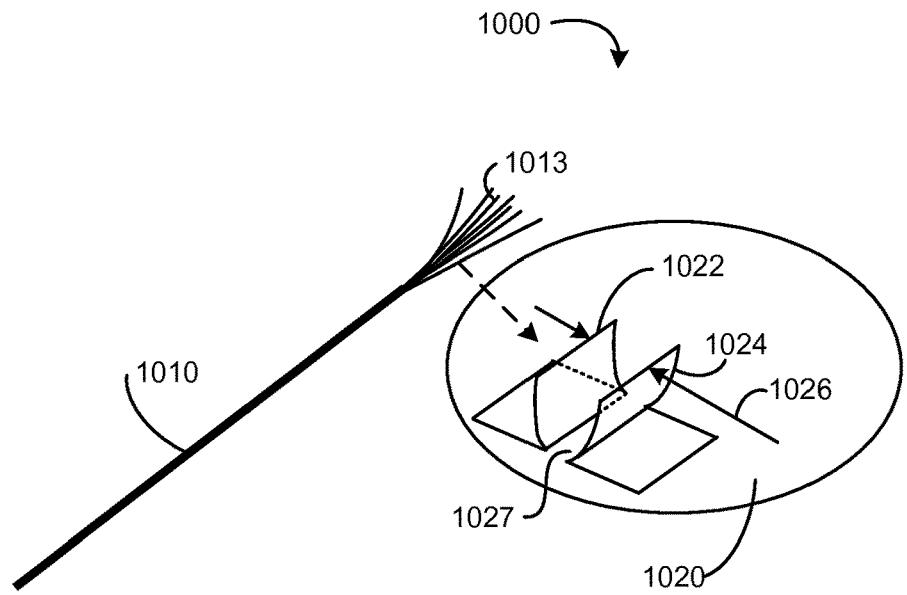
FIGS. 10A-10B depict an anchor connector for metallized film electrodes, according to an exemplary implementation.
Figure 10B:
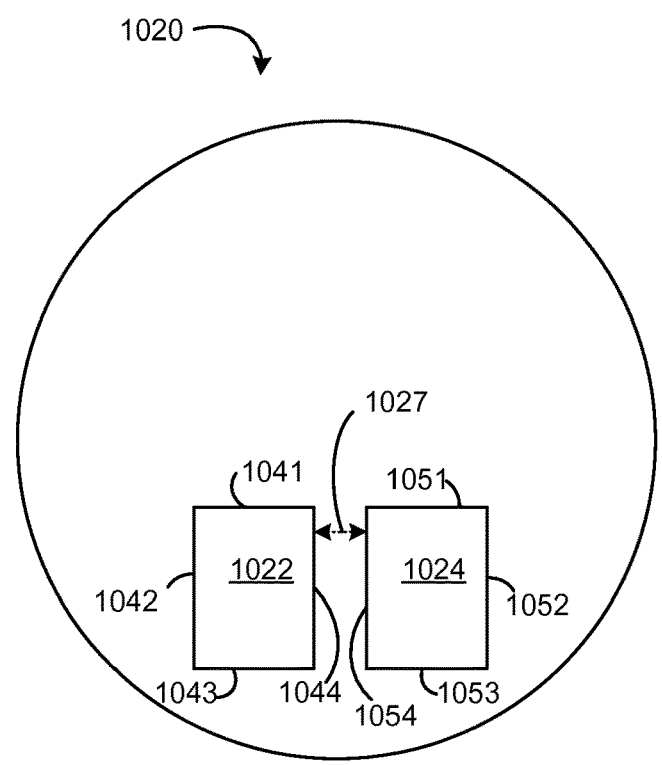

Additional variations in anchor connector designs are possible as shown in FIG. 10A and FIG. 10B. For example, FIG. 10A shows an exploded view of an embodiment of an anchor connector 1000 in which a metal anchor 1020 crimps onto an exposed metal core 1013 at a distal end of the lead wire 1010. FIG. 10B shows a corresponding top view of the metal anchor 1020. In this embodiment, the metal anchor 1020 has two rectangular cut-out flaps 1022 and 1024. In FIG. 10B, the flaps 1022, 1024 are flattened so they are flush with the top surface of the anchor 1020. In FIG. 10A, the flaps are bended upwards. The first flap 1022 is cut on three sides 1041, 1042, and 1043, and bended upwards along a forth side 1044.

In an embodiment, the second flap 1024 is cut on three sides 1051, 1052, and 1053, and bended upwards along a forth side 1054. The fourth side 1044 of the first flap 1022 is adjacent to the fourth side 1054 of the second flap 1024, with a spacing 1027 in between. Both the first flap 1022 and the second flap 1024 may be bent upward to form a wire channel 1026, sized to accept the distal end of the lead wire 1010. The distal end of the lead wire 1010 may be stripped of its insulation to expose a metal core 1013, which is a bundle of strands of small gauged wires, as shown. The metal core strands 1013 are inserted into the wire channel 1026, in between the cut-out flaps 1022 and 1024, and above the spacing 1027. The cut-out flaps 1022 and 1024 are then folded towards each other and towards the spacing 1027, on top of the metal core 1013 on the distal end 1012 of the lead wire 1010, to mechanically secure the distal end 1012 between the cut-out flaps 1022 and 1024 and the anchor 1020.

A proximal end of the lead wire 1010 may be electrically coupled to an electrostimulation device. For example, the proximal end of the lead wire 1010 many include a female socket, configured to receive a male pin on another lead wire connected to an electrostimulation device. As another example, the proximal end of the lead wire 1010 may include a male pin, to be inserted into a female socket on an electrostimulation device, or on another lead wire connected to an electrostimulation device. Since the lead wire 1010 is in electrical contact with the anchor 1020, a current is delivered through the lead wire to the anchor 1020 from the electrostimulation device. Mechanical crimping of the lead wire 1010 by the anchor 1020 through the use of cut-out flaps 1022 and 1024 provides a solder-less connection between the lead wire 1010 and the metal anchor 1020, offering increased pull strength that prevents the lead wire 1010 from being separated from the metal anchor 1020, once crimped in place. The assembled anchor connector 1000 may then be soldered or otherwise electrically coupled to a metal-coated area on a metallized film electrode such as those discussed herein, and currents delivered to the anchor connector 1000 are dispersed over the surface of the metal-coated area.

Figure 11A:
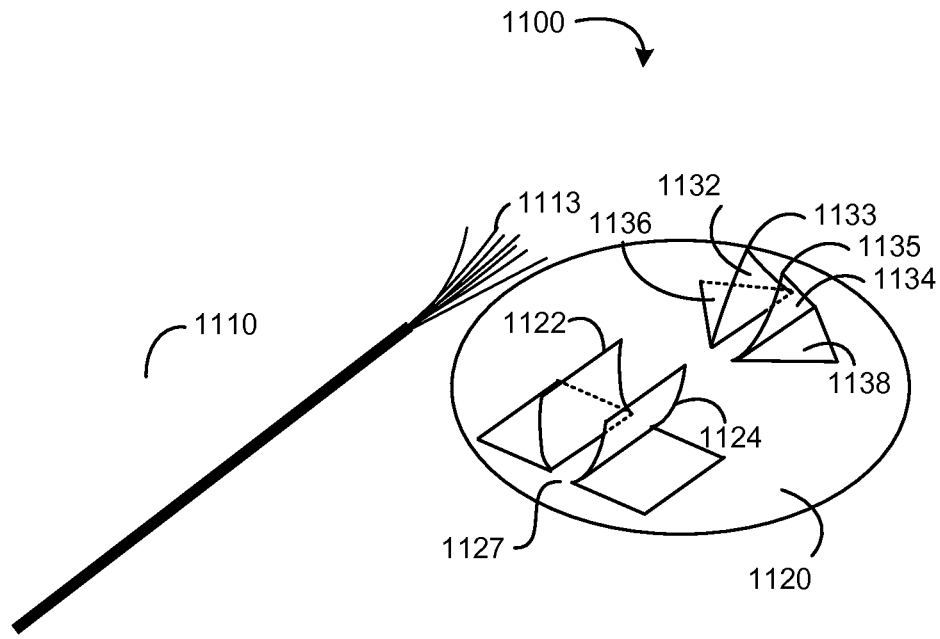
FIGS. 11A-11B depict a pinching anchor connector for metallized film electrodes, according to an exemplary implementation.
Figure 11B:
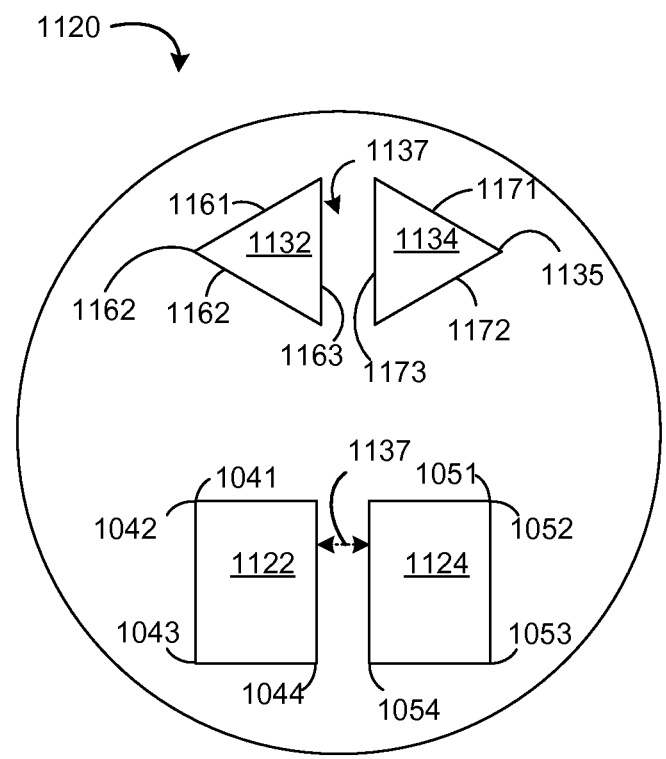

FIG. 11A shows an exploded view of another embodiment of a crimping or pinching anchor connector 1100. In addition to the cut-out flaps 1122 and 1124, substantially similar to the flaps 1022, 1024 of FIG. 10, the pinching anchor connector 1100 may comprise a pinching anchor 1120 and a second set of cut-out flaps 1132 and 1134. FIG. 11B depicts a top view of the second set of triangular flaps 1132, 1134, flattened to lie flush with the top surface of the pinching anchor 1120. FIG. 11A and FIG. 11B will be referred to in conjunction for the following discussion.

In FIG. 11A, the triangular flaps 1132, 1134 may be bended upwards to "stand" roughly orthogonal to the pinching anchor 1120. In this embodiment, both of the triangular flaps 1132, 1134 may be triangle shaped, and more specifically, equilateral triangle shaped. The first triangular flap 1132 is cut on two sides 1161 and 1162, and bended upwards along a third side 1163, creating a first aperture 1136 (FIG. 11A). The second triangular flap 1134 is cut on two sides 1171 and 1172 and is bended upwards along a third side 1173, creating a second aperture 1138. The third side 1163 of the first triangular flap 1132 is adjacent to the third side 1173 of the second triangular flap 1134, with a spacing 1137 in between. In this embodiment, the triangular flaps 1132 and 1134 have sharp corners 1133 and 1135 that may puncture the metallized film (not shown) when the metallized film is pressed onto the standing triangular flaps 1132, 1134. Portions of the triangular flaps 1132 and 1134 that protrude above a top surface of the metallized film from the bottom may be folded towards each other and the spacing 1137, to mechanically secure the pinching anchor connector 1120 to the metallized film. Portions of the triangular flaps 1132 and 1134 that protrude above the top surface of the metallized film may also be pressed back towards the apertures 1136 and 1138, in a clipping action to mechanically secure the anchor connector 1120 to the metallized film.

In some embodiments, less than two or more than two triangular flaps with sharp corners may be cut out from the pinching anchor 1120, similar to the triangular flaps 1132 and 1134 shown in FIG. 11A, to mechanically secure the pinching anchor connector 1120 to the metallized film, thus serving as pinch connectors to the metallize film electrode. The cut-out flaps 1132, 1134 may be configured to have shapes different from equilateral triangles. In some embodiments, portions of the cut-out flaps that protrude above a top surface of the metallized film may be covered by an additional non-conductive layer, such as a small piece of non-conductive tape, to prevent unintentional current leakages through the back of the electrode.

By using a pinching anchor connector 1100 as shown in FIGS. 11A and 11B, soldering can be eliminated, simplifying the electrode assembly process, and reducing manufacturing cost. Since the soldering process adds additional metal material, using an anchor connector may also reduce overall electrode profile and weight. The attachment of anchor connectors to metallized film electrodes may be automated during the manufacturing process. In other embodiments, because attachment and removal of pinching anchor connectors from metallized films can be performed manually by a clinician or the patient, pinching anchor connectors may be reused with pre-packaged metallized films to create disposable metallized film electrodes.

Figure 22:
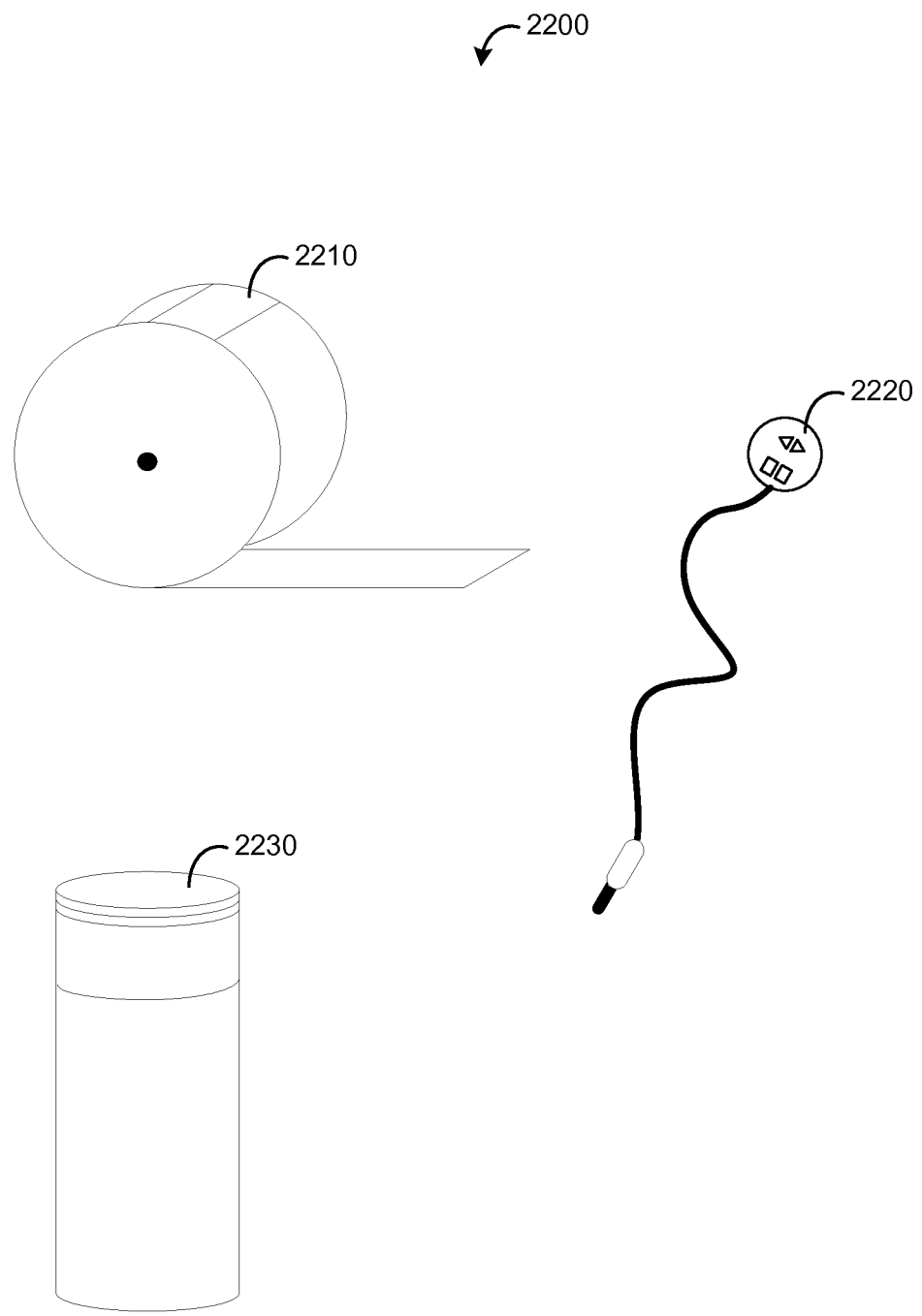
FIG. 22 shows a metallized film electrode kit, according to an exemplary implementation.

As a non-limiting example, FIG. 22 shows an illustrative embodiment of a metallized film electrode kit 2200. The metallized film electrode kit 2200 comprises a roll 2210 of metallized film strips substantially similar to those discussed with reference to FIG. 4 and FIG. 5, an anchor connector 2220 as discussed with reference to FIG. 11A and FIG. 11B, and a hydrogel dispenser 2230 as discussed with reference to FIG. 2A and FIG. 2B. In some embodiments, the metallized film electrode kit 2200 may contain metallized film sheets instead of the roll 2210. The hydrogel dispenser 2230 may be a roll-on applicator, a spray bottle, or other dispensing means. The metallized film electrode kit 2200 may further comprise single-sided or double-sided non-conductive adhesive tapes (not shown), and/or elastic straps with fastening means to secure metallized film electrodes to a desired part of the body. In addition to snap, magnetic, and anchor connectors, other variations in connector design are possible.

Figure 12:
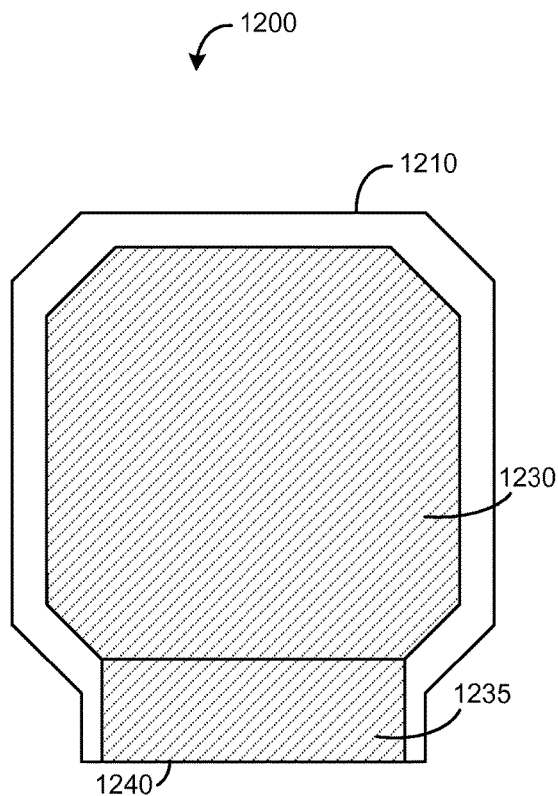
FIG. 12 is a bottom view of a metallized film tab electrode, according to an exemplary implementation.

FIG. 12 shows a bottom view of a metallized film tab electrode 1200. A first metal-coated area 1230 extends on one side into a second metal-coated area 1235, which further extends to an edge 1240 of a base layer 1210. In some implementations of the tab electrode 1200, the first metal-coated area 1230 is coupled with a conductive gel layer for dispersing current into the patient's tissue. The second-coated area 1235 functions as a tab connector, onto which an electrically conductive pinch connector or an alligator clip electrically coupled to an electrostimulation device can be fastened.

In some embodiments of metallized film electrodes, a conductive pinch connector (not shown) or an alligator clip may be attached to the first metal-coated area directly to establish electrical connections to an electrostimulation device.

Figure 13:
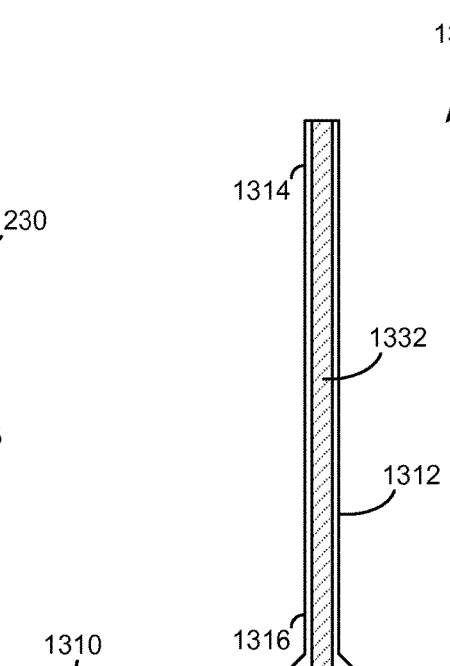
FIG. 13 is a bottom view of a metallized film unibody electrode, according to an exemplary implementation.
Figure 13:
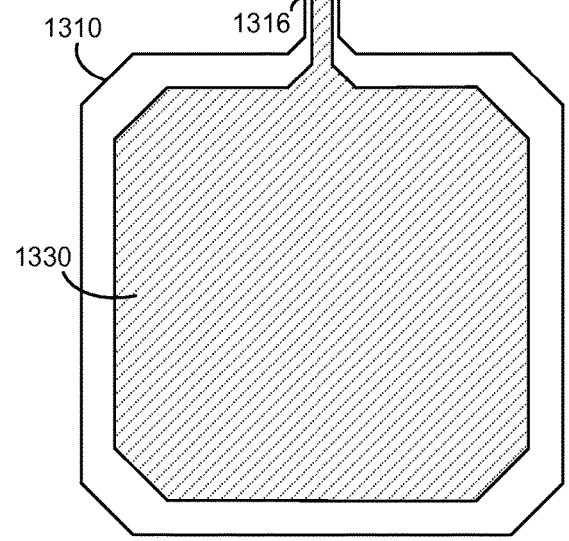

FIG. 13 shows a bottom view of a metallized film unibody electrode 1300, according to an illustrative embodiment. The structures of general unibody electrodes are disclosed in PCT Publ. No. WO2013/012465, the contents of which are hereby incorporated by reference in their entirety. The metallized film unibody electrode 1300 includes a body 1310 and a unitary tail 1312 which has a proximal end 1314 and a distal end 1316. The distal end 1316 extends into the body 1310. A first metal-coated area 1330 is included in the body 1310, and a second metal-coated area 1332 is included in the unitary tail 1312. The second metal-coated area 1332 is a unitary extension of the first metal-coated area 1330. The distal end 1314 of the electrode 1300 is configured to couple with a lead from an electrostimulation device (not shown), thereby coupling the first metal-coated area 1330 to the electrostimulation device so that electrostimulation current may be applied to a patient's tissue through the electrode 1300.

Figure 14:
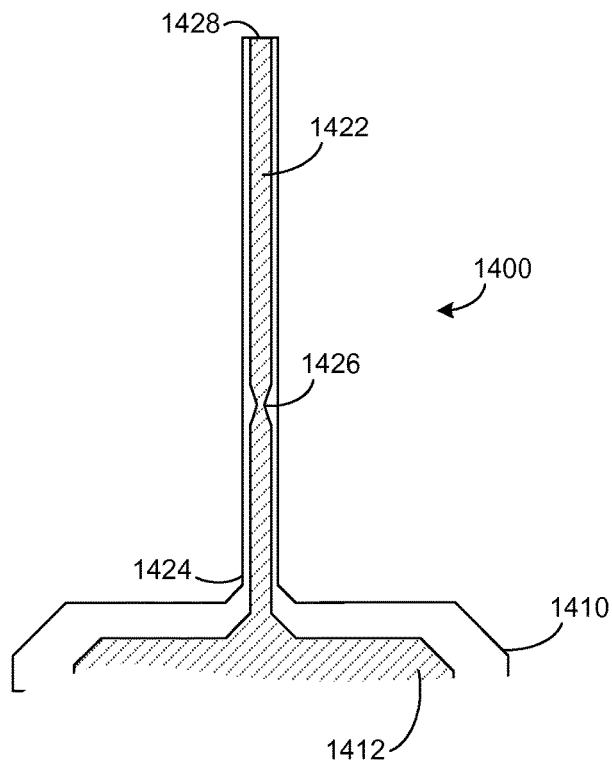
FIGS. 14 and 15 are bottoms views of unitary tails of metallized film unibody electrodes, according to an exemplary implementation.
Figure 15:
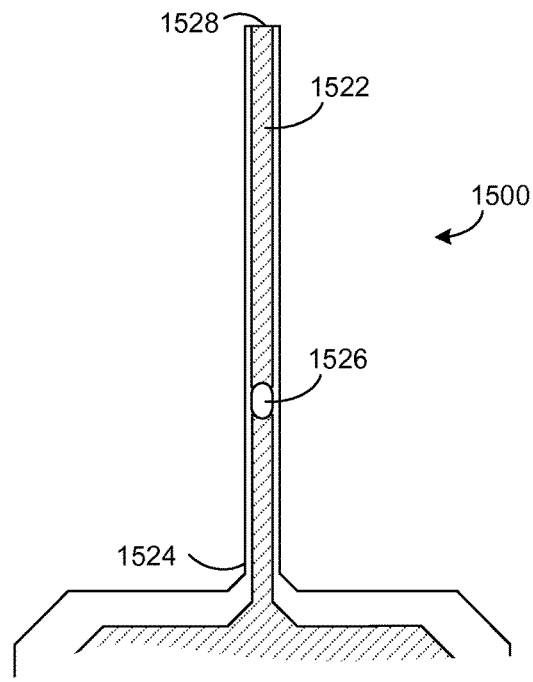

FIG. 14 and FIG. 15 show bottom views of illustrative unitary tails of metallized film unibody electrodes, for example, unibody electrode 1300 (FIG. 13). In the embodiment shown in FIG. 14, a tail 1400 is a unitary extension of a body 1410. The body 1410 comprises a first metal-coated area 1412; the unitary tail 1400 comprises a second metal-coated area 1422, a unitary extension of the first metal-coated area 1412. The second metal-coated area 1422 includes a connection point 1426, connecting a distal portion 1424 and a proximal portion 1428 of the second metal-coated area 1422. In the longitudinal direction, the width of the second metal-coated area 1422 changes from proximal to distal ends, reaching a minimum "pinch point" at the connection point 1426, such that the cross-sectional area of the metal coating at the connection point 1426 is smaller or narrower than at other points along the longitudinal extension of the second metal-coated area 1422. The smaller cross-sectional area at the connection point 1426 concentrates the current density at the connection point 1426. This change in the width can have safety benefits. For example, in some embodiments, the width of second metal-coated area 1422 at the connection point 1426 is configured to cause the metal coating to melt when current density passing through the connection point 1426 is higher than a threshold value, thus electrically disconnecting the metallized electrode from the electrostimulation device. The connection point 1426 serves as a fuse for the electrode. In some embodiments, the thickness of the metal coating at the connection point 1426 is varied to modulate the cross-sectional area at the connection point 1426 and the density of current passing through the connection point 1426.

In FIG. 15, an embodiment of unitary tail 1500 comprises a connection point 1526 formed by a material different from a distal portion 1524 and a proximal portion 1528 of a metal-coated area 1522 on the unitary tail 1500. In an embodiment, the material comprising the connection point 1526 has lower conductive properties than that of the rest of the metal-coated area 1522, thus failing under an electrical current load at a certain threshold. The connection point 1526 thus provides fuse-like functionality, substantially similar to connection point 1426 (FIG. 14).

Figure 16:
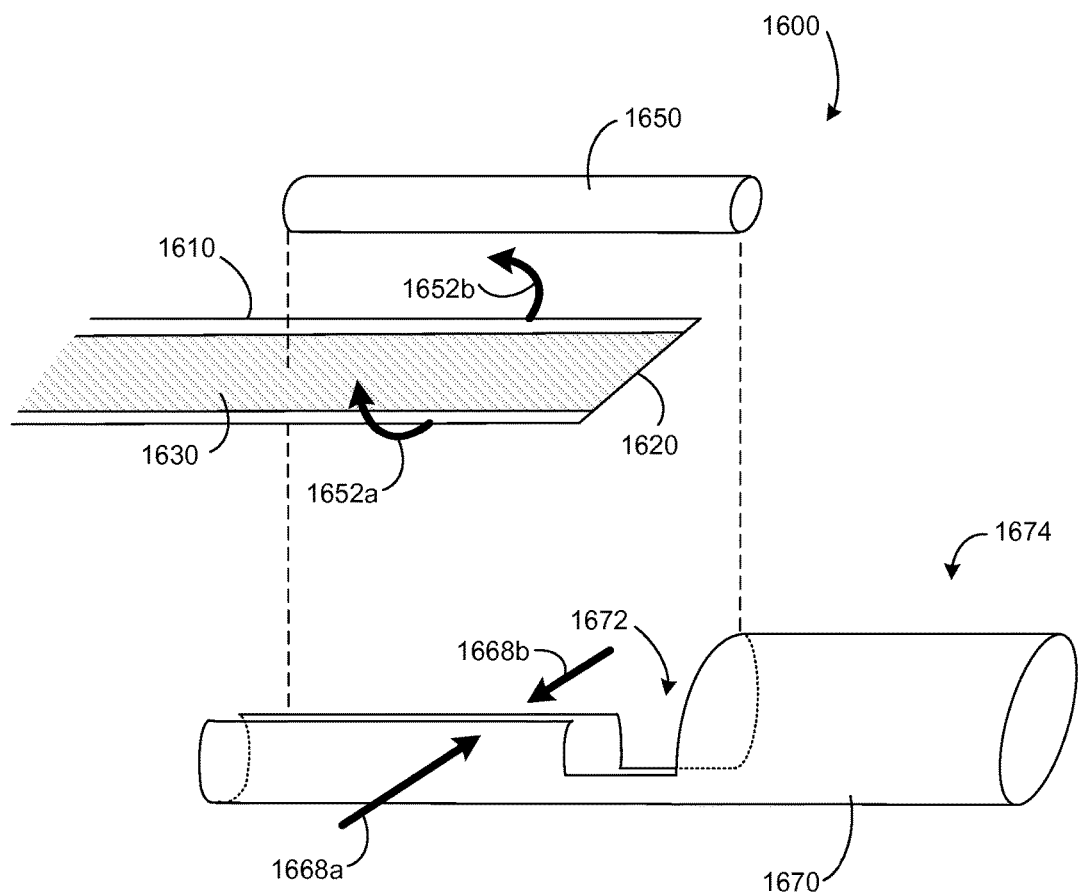
FIG. 16 is an exploded view of a crimp connector to a metallized film unibody electrode, according to an exemplary implementation.

FIG. 16 shows an exploded view of a crimp connector 1600 for electrically coupling a proximal end 1620 of a unitary tail 1610 through a lead wire (not shown) to an electrostimulation device. The crimp connector comprises a metal crimp pin 1670 and a segment 1650 of conductive wire. In some embodiments, the diameter of the wire segment 1650 is less than about 0.08 inches. In some embodiments, the diameter of the wire segment 1650 is less than about 0.005 inches. The wire segment 1650 may have round or oval-shaped cross sections. In FIG. 16, the proximal end 1620 of the unitary tail 1610 is shown with the metal coating 1630 facing up. In some embodiments, the unitary tail 1610 may be configured to have the metal coating 1630 facing down, towards the crimp pin 1670. The proximal end 1620 of the unitary tail 1610 is disposed at least partially below the wire segment 1650 and folded around the longitudinal axis of the wire segment 1650 as shown by two arrows 1652a, 1652b. The wire segment 1650, once wrapped in the metallized film, is inserted into a wire channel 1672 on a distal end of the metal crimp pin 1670. Crimping action across the wire channel 1672 in the direction indicated by arrows 1668a, 1668b, establishes a mechanically secure connection between the unitary tail 1610 and the metal crimp pin 1670, and provides pull strength between the unitary tail 1610 and the crimp connector. In embodiments where the metal coating 1630 faces the wire segment 1650, at least a portion of the wire segment 1650 is also configured to touch the crimp pin 1670 directly. In embodiments where the metal coating 1630 faces the crimp pin 1670, the metal coating 1630 touches the crimp pin 1670 directly once the wire segment 1650 and the proximal end 1620 of the unitary tail 1610 are crimped into the wire channel 1672. Direct contacts between the metal coating 1630, the conductive wire segment 1650, and the metal crimp pin 1670 establish an electrical connection between the unitary tail 1610 and the metal crimp pin 1670.

The crimp pin 1670 shown in FIG. 16 may further include a female socket 1674 on the proximal end, for receiving a male pin (not shown) from a lead wire connected to an electrostimulation device. In some embodiments, the crimp pin 1670 may include a male pin on the proximal end, configured to couple with a female socket on a lead wire connected to an electrostimulation device. In embodiments where the unitary tail 1610 is long enough to serve as an electrical lead, a male pin on the proximal end of the crimp pin 1670 may be coupled to a female socket on an electrostimulation device. For example, when a portable electrostimulation device is attached to the patient's body, close to the desired treatment site, the crimp pin 1670 may connect to the electrostimulation device directly.

In some embodiments, the crimp connector 1600 is further enclosed in a non-conductive housing (not shown) to avoid current leakage. For example, once the proximal end 1620 of the unitary tale 1610 and the crimp connector have been brought into proximity, a heat-shrink tubing (not shown) may be positioned over the crimp connector, extending onto the unitary tail 1610 beyond the crimp connector. When heat is applied, the heat-shrink tubing may conform to the unitary tail 1610 and to the crimp pin. The heat-shrunk tubing then provides mechanical support to the crimp pin and the unitary tail 1610, as well as electrical insulation between the crimp connector and a user of the electrode.

One advantage of the crimp connector 1600 shown in FIG. 16 is its ability to improve the pull-strength of the connection. By including a wire segment 1650, the crimp pin 1670 can bite into the wire segment 1650 without pinching through the metallized film. By comparison, a pinch connector that bites directly onto the unitary tail or the body of the electrode may cause the metallized film electrode to rip when the connector is inadvertently pulled, especially when the base layer is made of a material with low tensile strength.

Another advantage of the crimp connector shown in FIG. 16 is its low-profile. With a thin wire segment 1650 and a small crimp pin 1670, the overall profile of the connector may be made small. Low-profile metallized film electrodes with low-profile connectors can be adhesively attached or strapped unto the patient's body under clothing, possibly with a portable electrostimulation device, without interfering with the patient's general physical activities or compromising patient comfort.

Figure 20:
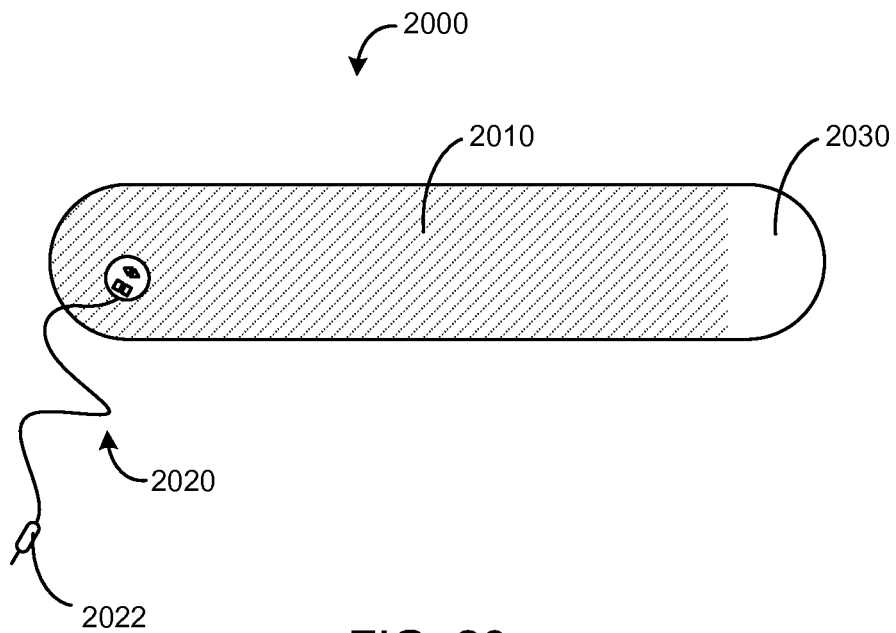
FIG. 20 shows a lower back belt made with metallized textile, according to an exemplary implementation.
Figure 21:
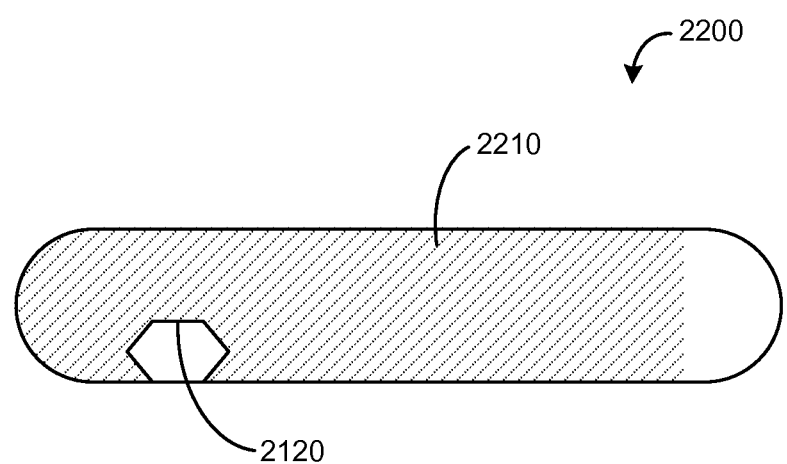
FIG. 21 shows another lower back belt made with metallized textile, according to an exemplary implementation.

FIG. 20 and FIG. 21 show illustrative embodiments of electrostimulation systems assembled from devices aforementioned in the present disclosure. FIG. 20 shows a lower back belt 2000 made of a metallized textile. A pinching anchor connector 2020, substantially similar to the pinching anchor connector 1100, is fixed to a metal-coated area 2010 near a first end of the belt 2000. An uncoated area 2030 is located near a second end of the belt 2000, opposite to the first end. The belt 2000 may further comprise a fastening means for securing the belt onto the patient's lower back. For example, the uncoated area 2030 may be covered with an adhesive or Velcro. Regular buttons or snap buttons may also be used. In some embodiments, the metal-coated area 2010 may extend to the edge of the second end of the belt. The pinching anchor connector 2020 pinches through the metallized textile to form a mechanically secure and electrically conductive connection to the belt. A proximal end 2022 of the pinching anchor connector 2020 includes a male pin that can be coupled with a female socket on an electrostimulation lead (not shown). In different embodiments, other types of connectors such as alligator clips and snap connectors may be used instead of the pinching anchor connector.

FIG. 21 shows an illustrative metallized textile lower back belt electrostimulation system. In this embodiment, a portable electrostimulation device 2120 is attached directly to a metal-coated area 2210 to provide signals for electrostimulation. In other embodiments, the portable electrostimulation device 2120 may be positioned on the other side of the metallized textile.

Figure 23A:
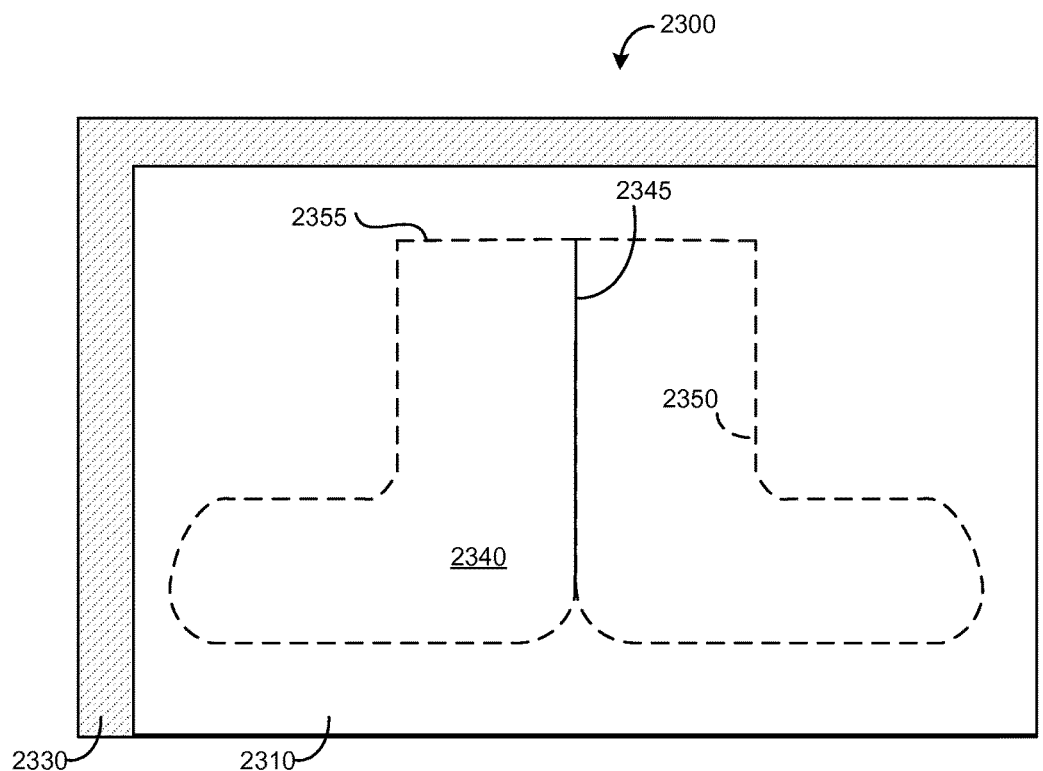
FIG. 23A shows a metallized fabric, according to an exemplary implementation.
Figure 23B:
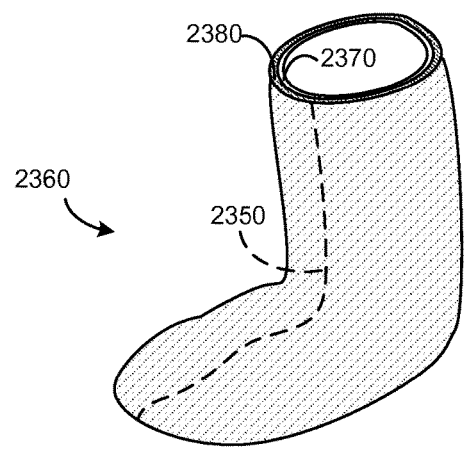
FIG. 23B shows a wearable sock electrode, according to an exemplary implementation.

FIG. 23A shows a top view of an illustrative metallized fabric 2300 that can be cut and sewed into a wearable sock electrode 2360 shown in FIG. 23B. In an embodiment, the metallized fabric 2300 is manufactured by depositing a metal coating 2310 onto a woven fabric base layer 2300. A piece 2340 can be cut out from the metallized fabric 2300 along the dotted line 2350, then folded along the line 2345 to obtain two layers of metallized fabrics. By sewing along all edges of the cut-out piece 2340 but a top edge 2355, a wearable sock electrode 2360 as shown in FIG. 23B is obtained, where a metal coating 2370 is positioned on an inner surface of the sock electrode 2360. The fabric base layer 2380 is positioned on an outer surface of the sock electrode 2360, forming a sock. The metal coating 2370 is electrically connected to an electrostimulation device through a connector (not shown), and electrostimulation signals can be applied to the sock. Different types of connectors such as pinch or magnetic connectors may be used in different embodiments.

According to different examples, a wearable sock electrode 2360 may be worn by diabetic patients with peripheral circulatory disorders to reduce edema and pain. A wearable sock electrode 2360 may also be used to treat other medical conditions such as arthritis and peripheral neuropathy. Other garment electrodes may be produced from metallized fabrics in a similar fashion, in the form of gloves, tank tops, shirts, knee guards, among others. In addition to its ease of use and its ability to provide large contact areas for treatment, in some applications, garment electrodes constructed of metallized textiles may be worn without the use of a gel. Sweat naturally produced during exercise may contain sufficient amount of ions to facilitate current transfer across the interface between the metal coating and the skin.

It is to be understood that the foregoing is merely illustrative, and is not to be limited to the details given herein. While several embodiments have been provided by the present disclosure, it should be understood that the disclosed systems and devices and their components may be embodied in any other specific forms without departing from the scope of the disclosure.

Variations and modifications will occur to those of skill in the art after reviewing this disclosure, where disclosed features may be implemented in any combination and subcombinations (including multiple dependent combinations and subcombinations), with one or more other features described herein. The various features described or illustrated above, including any components thereof, may be combined or integrated in other devices, systems, or methods; moreover, certain features may be omitted or not implemented.

Examples of changes, substitutions, and alternations are ascertainable by one skilled in the art and to be made without departing from the scope of the information disclosed herein.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Where a range of values is provided, it is understood that the upper and lower limit, and each intervening value between the upper and lower limit of the range is encompassed within the embodiments.

The mere fact that certain measures are recited in mutually different dependent claims does not indicate that a combination of these measures cannot be used to advantage. Any reference signs in the claims should not be construed as limiting the scope.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing dimensions, thicknesses, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

What is claimed is:

1. An electrode for noninvasive electrotherapy, comprising:
   a metallized film having a base layer and a metal coating disposed on a bottom surface of the base layer, the metallized film having a first metal-coated area configured for application of therapeutic electrical stimulation to a patient's tissue, wherein a circumference of the first metal-coated area is approximately coextensive with a perimeter of the base layer, wherein the metal coating consists of particles of metal deposited by physical vapor deposition, and wherein the base layer further comprises a tail having a third metal-coated area and a second metal-coated area configured as a unitary extension of the first metal-coated area, wherein the second metal-coated area is situated between the third metal-coated area and the first metal-coated area and is configured to provide a fuse-like functionality;
   a gel layer disposed beneath the first metal-coated area, wherein the gel layer extends around a side of the metallized film to cover perimeter side surfaces of the metal coating; and
   a connector configured to provide electrical communication to the first metal-coated area, wherein the connector comprises a metal anchor and a lead wire, wherein the metal anchor is disposed beneath the first metal-coated area and wherein the lead wire is configured to provide electrical communication to the metal anchor, the lead wire comprising a metal core and an insulating layer, wherein a first end of the metal core is disposed between the metal anchor and a bottom surface of the first metal-coated area, and wherein the metal anchor is a same type of metallic material as used for the metal coating, and is configured to drive current input from the lead wire through a path of least resistance to the metal coating instead of the gel layer,
   wherein a width of the second metal-coated area changes from the proximal end of the second metal-coated area to the distal end of the second metal-coated area and reaches a minimum pinch point at a connection point, wherein a cross-sectional area of a metal coating at the connection point is smaller or narrower than at other points along a longitudinal extension of the second metal-coated area, such that the smaller cross-sectional area at the connection point is configured to concentrate a current density at the connection point.

2. The electrode of claim 1, wherein the base layer is selected from the group consisting of nonconductive, semiconductive, and polymeric.

3. The electrode of claim 1, wherein the base layer comprises polyurethane.

4. The electrode of claim 1, wherein the base layer is a woven textile.

5. The electrode of claim 1, wherein the base layer is a nonwoven fabric.

6. The electrode of claim 1, wherein the base layer is vapor permeable.

7. The electrode of claim 1, wherein the base layer is porous.

8. The electrode of claim 1, wherein the bottom surface of the base layer includes a plurality of dimples or mounds.

9. The electrode of claim 1, wherein the metal-coating is pure aluminum.

10. The electrode of claim 1, wherein the metal-coating comprises a metal selected from the group consisting of silver, gold, an aluminum alloy, and an aluminum compound.

11. The electrode of claim 1, wherein a distance between a first point on a bottom surface of the metal coating and a second point on the bottom surface of the base layer defines a thickness of the metal coating at the first point, wherein a line connecting the first point and the second point extends vertically through a cross-section at the first point, and wherein the metal coating has a maximum thickness of 0.01 μm to 0.2 μm.

12. The electrode of claim 1, wherein the metal coating has a maximum thickness of 20 μm or less and wherein the base layer has a maximum thickness of 0.00001 inches to 0.005 inches.

13. The electrode of claim 1, further comprising a plurality of metal-coated areas, the plurality of metal-coated areas being electrically isolated and spaced apart.

14. The electrode of claim 1, wherein a thickness of the metal coating is non-uniform across the first metal-coated area.

15. The electrode of claim 1, wherein a width of the third metal-coated area varies from a proximal end of the tail to a distal end of the tail, wherein the third metal-coated area comprises a connection point that bridges a proximal portion of the third metal-coated area and a distal portion of the third metal-coated area, wherein the connection point is of a metal different from the metal coating, further comprising a nonconductive layer disposed along the tail, beneath the third metal-coated area, wherein the connector comprises:
   a conductive wire segment disposed along a proximal end of the tail, wherein at least a portion of the conductive wire segment is in contact with the third metal-coated area;
   a metal crimp pin, wherein a distal end of the crimp pin is configured to crimp onto the conductive wire segment and the proximal end of the tail, and a proximal end of the crimp pin is configured to receive a male pin from an electrostimulation lead; and
   a nonconductive housing configured to enclose the metal crimp pin.

16. The electrode of claim 1, wherein the gel layer has a maximum thickness of 0.001 inches to 0.1 inches, and wherein a combined thickness of the metallized film and the gel layer has a maximum value of 0.001 inches to 0.05 inches.

17. The electrode of claim 1, wherein the width of second metal-coated area at the connection point is configured to cause the metal coating to melt when the current density passing through the connection point is higher than a threshold value, thereby electrically disconnecting the electrode from an electrostimulation device.

18. The electrode of claim 1, wherein a thickness of the metal coating at the connection point is varied to modulate the cross-sectional area at the connection point and the current density passing through the connection point.

19. An electrode for noninvasive electrotherapy, comprising:
- a metallized film having a base layer and a metal coating disposed on a bottom surface of the base layer, the metallized film having a first metal-coated area configured for application of therapeutic electrical stimulation to a patient's tissue, wherein a circumference of the first metal-coated area is approximately coextensive with a perimeter of the base layer, wherein the metal coating consists of particles of metal deposited by physical vapor deposition, and wherein the base layer further comprises a tail having a third metal-coated area and a second metal-coated area configured as a unitary extension of the first metal-coated area, wherein the second metal-coated area is situated between the third metal-coated area and the first metal-coated area and is configured to provide a fuse-like functionality;
- a gel layer disposed beneath the first metal-coated area, wherein the gel layer extends around a side of the metallized film to cover perimeter side surfaces of the metal coating; and
- a connector configured to provide electrical communication to the first metal-coated area, wherein the connector comprises a metal anchor and a lead wire, wherein the metal anchor is disposed beneath the first metal-coated area and wherein the lead wire is configured to provide electrical communication to the metal anchor, the lead wire comprising a metal core and an insulating layer, wherein a first end of the metal core is disposed between the metal anchor and a bottom surface of the first metal-coated area, and wherein the metal anchor is a same type of metallic material as used for the metal coating, and is configured to drive current input from the lead wire through a path of least resistance to the metal coating instead of the gel layer, wherein a width of the third metal-coated area varies from a proximal end of the tail to a distal end of the tail, wherein the third metal-coated area comprises a connection point that bridges a proximal portion of the third metal-coated area and a distal portion of the third metal-coated area, wherein the connection point is of a metal different from the metal coating, further comprising a nonconductive layer disposed along the tail, beneath the third metal-coated area, wherein the connector comprises:
- a conductive wire segment disposed along a proximal end of the tail, wherein at least a portion of the conductive wire segment is in contact with the third metal-coated area;
- a metal crimp pin, wherein a distal end of the crimp pin is configured to crimp onto the conductive wire segment and the proximal end of the tail, and a proximal end of the crimp pin is configured to receive a male pin from an electro stimulation lead; and
- a nonconductive housing configured to enclose the metal crimp pin, wherein the metal comprising the connection point has a lower conductive property than that of the rest of the metal-coated areas, wherein the connection point is configured to fail under an electrical current load at a threshold value.

* * * * *